(12) United States Patent
Tobler et al.

(10) Patent No.: US 6,294,504 B1
(45) Date of Patent: Sep. 25, 2001

(54) HERBICIDAL COMPOSITION

(75) Inventors: Hans Tobler, Allschwil; Henry Szczepanski, Wallbach; Werner Föry, Riehen, all of (CH)

(73) Assignee: Syngenta Crop Protection, Inc., Greensboro ( * ) Notice: Subject to any disclaimer, the term of this patent is extended or adjusted under 35 U.S.C. 154(b) by 0 days.

(21) Appl. No.: 09/269,453

(22) PCT Filed: Sep. 24, 1997

(86) PCT No.: PCT/EP97/05252

§ 371 Date: Jun. 24, 1999

§ 102(e) Date: Jun. 24, 1999

(87) PCT Pub. No.: WO98/13361

PCT Pub. Date: Apr. 2, 1998

(30) Foreign Application Priority Data

Sep. 26, 1996 (CH) .................................................. 2359/96

(51) Int. Cl.[7] ........................ A01N 43/40; A01N 43/647; C07D 343/00; C07D 335/04
(52) U.S. Cl. ........................ 504/246; 504/288; 504/261; 504/292; 504/307; 549/14; 549/23
(58) Field of Search .................................. 504/246, 288, 504/261, 292, 307; 549/14, 23

(56) References Cited

U.S. PATENT DOCUMENTS

| | | |
|---|---|---|
| 4,895,590 | 1/1990 | Hartzell . |
| 5,002,606 | 3/1991 | Moser et al. . |
| 5,009,699 | 4/1991 | Brady et al. . |
| 5,209,771 | 5/1993 | Meyer . |
| 5,591,694 | 1/1997 | Hamprecht et al. . |

FOREIGN PATENT DOCUMENTS

| | | |
|---|---|---|
| 4 128 441 | 3/1993 | (DE) . |
| 4128441 * | 4/1993 | (DE) . |
| 0496701 * | 1/1992 | (EP) . |
| 0 477 808 | 4/1992 | (EP) . |
| 0 496 701 | 7/1992 | (EP) . |
| 2 686 880 | 8/1993 | (FR) . |
| 92/08703 | 5/1992 | (WO) . |
| 96/11574 | 4/1996 | (WO) . |

OTHER PUBLICATIONS

Tetrahedron Letters No.21, K. Wiedhaup et al Formylation of Cyclic, pp. 1599–1605, 1965.*
Friedhelm korte und Karl Heinz Buchel, p. 1021–1025, 1960.*
Communications, Anthony Marfat An Improved Akylation . . . p. 515, May 1987.*
Chem. Ber. 93, pp. 1021–1025 (1960) (English translation enclosed).
Chem. Ber. 107, pp. 739–744 (1974) (English language abstract on front page).
Tetrahedron Lett., No. 21, pp. 1599–1605 (1965).
Tetrahedron Lett., vol. 32, No. 7, pp. 851–854 (1991).
Z. Naturforsch. B, 34B(2), pp. 283–289 (1979).
Heterocycles, vol. 35, No. 1, pp. 305–313 (1993).
J. Heterocyclic Chem. 20, 811–812 (1983).
J. Heterocyclic Chem. 32, pp. 73–77 (1995).
J. Chem. Soc. 101, pp. 2542–2552 (1912).
J. Org. Chem. 15, pp. 1135–1138 (1950).
Synthesis 1987, pp. 515–517.
Brighton Crop Protection Conf.—Weeds—1995 (Plenary Session 2, Nov. 21, 1995, Proceedings vol. 2, pp. 79–85).
Derwent Abstract 93–346962/44 (of FR 2 686 800).

* cited by examiner

*Primary Examiner*—Alan L. Rotman
*Assistant Examiner*—Rita Desai
(74) *Attorney, Agent, or Firm*—William A. Teoli, Jr.

(57) ABSTRACT

The present invention relates to new compounds of formula (I) wherein R1 to R3, U, V, W, Z and m have the significances given in the description, their use as antidotes, in herbicidal compositions for the control of weeds and plants in useful plant cultivation.

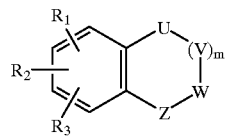

(I)

13 Claims, No Drawings

HERBICIDAL COMPOSITION

CROSS-REFERENCE

This application is a 371 of PCT/EP97/05252 filed Sep. 24, 1997.

The present invention relates to new antidotes, their use as antidotes in herbicidal compositions, these compositions and their usage in the control of grasses and weeds in cultivations of useful plants, especially in cultivations of maize, cereals, soybeans and rice.

The objects of the present invention are compounds of formula I

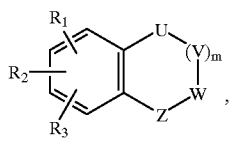

(I)

wherein $R_1$ is hydrogen, $C_1$–$C_4$-alkyl, $C_1$–$C_4$-alkyl substituted by $C_1$–$C_4$-alkyl-X- or $C_1$–$C_4$-halogen-alkyl-X-, $C_1$–$C_4$-halogen-alkyl, nitro, cyano, -COOR$_8$, —NR$_{11}$R$_{12}$, —SO$_2$NR$_{11}$R$_{12}$ or —CONR$_{13}$R$_{14}$;

$R_2$ is hydrogen, halogen, $C_1$–$C_4$-alkyl, trifluoromethyl, $C_1$–$C_4$-alkoxy or $C_1$–$C_4$-halogen-alkoxy;

$R_3$ is hydrogen, halogen or $C_1$–$C_4$-alkyl;

U, V, W and Z. independently of one another, are oxygen, sulphur, C(R$_{15}$)R$_{16}$, carbonyl, NR$_{17}$ or a group

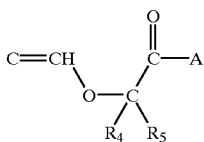

with the provisos that a) at least one of the ring members U, V, W or Z is carbonyl, and one ring member which is adjacent to this or these ring members signifies the group

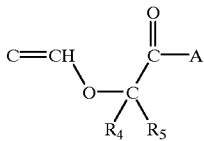

whereby this group only appears once; and b) two adjacent ring members U and V, V and W and W and Z cannot simultaneously signify oxygen;

$R_4$ and $R_5$, independently of one another, signify hydrogen or $C_1$–$C_8$-alkyl; or $R_4$ and $R_5$ together form a $C_2$–$C_6$-alkylene group;

A is $R_7Y$— or —NR$_{18}$R$_{19}$;

X is oxygen or —S(O)$_p$;

Y is oxygen or sulphur;

$R_7$ is hydrogen, $C_1$–$C_8$-alkyl, $C_1$–$C_4$-halogen-alkyl, $C_1$–$C_4$-alkoxy-$C_1$–$C_8$-alkyl, $C_3$–$C_6$-alkenyloxy-$C_1$–$C_8$-alkyl or phenyl-$C_1$–$C_8$-alkyl, whereby the phenyl ring may be substituted by halogen, $C_1$–$C_4$-alkyl, trifluoromethyl, methoxy or methyl-S(O)$_p$-; $C_3$–$C_6$-alkenyl, $C_3$–$C_6$-halogen-alkenyl, phenyl-$C_3$–$C_6$-alkenyl, $C_3$–$C_6$-alkinyl, phenyl-$C_3$–$C_6$-alkinyl, oxetanyl, furfuryl or tetrahydrofurfuryl;

$R_8$ is hydrogen or $C_1$–$C_4$-alkyl;

$R_9$ is hydrogen, $C_1$–$C_4$-alkyl or $C_1$–$C_4$-alkylcarbonyl;

$R_{10}$ is hydrogen or $C_1$–$C_4$-alkyl; or $R_9$ and $R_{10}$ together form a $C_4$- or $C_5$-alkylene group;

$R_{11}$, $R_{12}$, $R_{13}$ and $R_{14}$, independently of one another, are hydrogen or $C_1$–$C_4$-alkyl; or $R_{11}$ together with $R_{12}$ or $R_{13}$ together with $R_{14}$, independently of one another, are $C_4$- or $C_5$-alkylene, whereby one carbon atom may be replaced by oxygen or sulphur, or one or two carbon atoms may be replaced by —NR$_{15}$-;

$R_{15}$ and $R_{16}$, independently of one another, are hydrogen or $C_1$–$C_8$-alkyl; or $R_{15}$ and $R_{16}$ together are $C_2$–$C_6$-alkylene;

$R_{17}$ is hydrogen, $C_1$–$C_8$-alkyl, optionally substituted phenyl or benzyl optionally substituted on the phenyl ring;

$R_{18}$ is hydrogen, $C_1$–$C_8$-alkyl, phenyl, phenyl-$C_1$–$C_8$-alkyl, whereby the phenyl rings may be substituted by fluorine, chlorine, bromine, nitro, cyano, —OCH$_3$, $C_1$–$C_4$-alkyl or CH3SO$_2$-; $C_1$–$C_4$-alkoxy-$C_1$–$C_8$-alkyl, $C_3$–$C_6$-alkenyl, $C_3$–$C_6$-alkinyl or $C_3$–$C_6$-cycloalkyl;

$R_{19}$ is hydrogen, $C_1$–$C_8$-alkyl, $C_3$–$C_6$-alkenyl or $C_3$–$C_6$-alkinyl; or $R_{18}$ and $R_{19}$ together are $C_4$- or $C_5$alkylene, whereby one carbon atom may be replaced by oxygen or sulphur, or one or two carbon atoms may be replaced by —NR$_{20}$-;

$R_{20}$ is hydrogen or $C_1$–$C_4$-alkyl;

m is 0 or 1; and p signifies 0, 1 or 2, as well as agronomically compatible salts and stereoisomers of these compounds.

The proviso a) denotes compounds of formula I, wherein 1, 2 or 3 of the ring members U, V, W/ and/or Z, independently of one another, are carbonyl, and one ring member which is adjacent thereto is the group

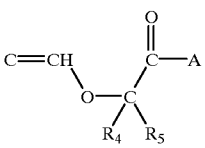

This group itself appears only once in the compound of formula 1. Therefore, in the proviso a), "one" is the numeral.

In the above-mentioned definitions, halogen is understood to be iodine and preferably fluorine, chlorine and bromine.

The alkyl, alkenyl and alkinyl groups appearing in the definitions of the substituents may be straight-chain or branched, and the same applies also to the alkyl, alkenyl and alkinyl moiety of the alkylcarbonyl, alkoxyalkyl, alkylthio and alkylsulphonyl groups.

Alkyl groups denote for example methyl, ethyl, n-propyl, iso-propyl, n-butyt, sec.-butyl, iso-butyl, tert.-butyl, as well as the various isomeric pentyl, hexyl, heptyl and octyl radicals. Methyl, ethyl, n-propyl, iso-propyl and n-butyl are preferred.

Examples of alkenyls which may be mentioned are allyl, methallyl, 1-methylvinyl, but-2-en-1-yl, pentenyl and 2-hexenyl, preferably alkenyl radicals with a chain length of 3 to 5 carbon atoms.

Examples of alkinyls which may be mentioned are propargyl, 1-methylpropargyl, 3-butinyl, but-2-in-1-yl, 2-methylbut-3-in-2-yl, but-3-in-2-yl, 1-pentinyl, pent-4-in-1-yl and 2-hexinyl, preferably alkinyl radicals with a chain length of 3 to 5 carbon atoms.

The halogen-alkyl which may be considered are alkyl groups that are substituted by halogen once or many times, especially once to three times, whereby halogen signifies in detail iodine and especially fluorine, chlorine and bromine, for example fluoromethyl, difluoromethyl, trifluoromethyl, chloromethyl, dichloromethyl, trichloromethyl, 2-fluoroethyl, 2,2-difluoroethyl, 2-chloroethyl, 2,2-dichloroethyl, 2,2,2-trifluoroethyl and 2,2,2-trichloroethyl.

Alkylsulphonyl is for example methylsulphonyl, ethylsulphonyl, propylsulphonyl, isopropyl-sulphonyl, n-butylsulphonyl, iso-butylsulphonyl, sec.-butylsulphonyl and tert.-butylsulphonyl; preferably methylsulphonyl and ethylsulphonyl.

Halogen-alkylsulphonyl is for example fluoromethylsulphonyl, difluoromethylsulphonyl, trifluoromethylsulphonyl, chloromethylsulphonyl, trichlommethylsulphonyl, 2-fluoroethyl-sulphonyl, 2,2,2-trifluoroethylsulphonyl and 2,2,2-trichloroethylsulphonyl.

Alkylcarbonyl is especially acetyl and propionyl.

Alkoxy is for example methoxy, ethoxy, n-propoxy, iso-propoxy, n-butoxy, iso-butoxy, sec.-butoxy and tert.-butoxy.

Alkenyloxy is for example allyloxy, methallyloxy and but-2-en-1-yloxy.

Alkinyloxy is for example propargyloxy and 1-methylpropargyloxy.

Alkoxyalkyl is for example methoxymethyl, methoxyethyl, ethoxymethyl, ethoxyethyl, n-propoxymethyl, n-propoxyethyl, iso-propoxymethyl and iso-propoxyethyl.

Halogenalkoxy is for example fluoromethoxy, difluoromethoxy, trifluoromethoxy, 2,2,2-trifluoro-ethoxy, 1,1,2,2-tetrafluoroethoxy, 2-fluoroethoxy, 2-chloroethoxy and 2,2,2-trichloroethoxy.

Of the alkenyl radicals that are substituted 1, 2 or 3 times by halogen, preference is given to those which have a chain length of 3 or 4 carbon atoms. The alkenyloxy groups may be substituted by halogen at saturated or unsaturated carbon atoms.

The halogen-alkenyloxy which may be considered are alkenyloxy groups that are substituted by halogen once or many times, whereby halogen signifies in detail bromine, iodine and especially fluorine and chlorine, for example 2- and 3-fluoropropenyloxy, 2- and 3-chloropropenyloxy, 2- and 3-bromopropenyloxy, 2,3,3-trifluoropropenyloxy, 2,3,3-trichloropropenyloxy, 4,4,4-trifluoro-but-2-en-1-yloxy and 4,4,4-trichloro-but-2-en-1-yloxy.

Alkylthio signifies for example methylthio, ethylthio, propylthio and butylthio, as well as the branched isomers thereof.

Phenyl or benzyl per se, or as part of a substituent, such as phenylalkyl or benzylamino, exist in optionally substituted form, in which case the substituents may be in ortho-, meta- or para-position. Substituents are e.g. $C_1$–$C_4$-alkyl, $C_1$–$C_4$-alkoxy, halogen, $C_1$–$C_4$-halogen-alkyl or $C_1$–$C_4$-halogen-alkoxy.

Corresponding significances may also be assigned to the substituents in compound definitions, such as alkyl-Y, halogen-alkyl-Y, alkoxy-alkyl-Y, alkenyloxy-alkyl-Y, phenyl-alkyl-Y, alkenyl-Y, halogen-alkenyl-Y, phenyl-alkenyl-Y, phenyl-alkinyl-Y, halogen-alkyl-X-alkyl and alkyl-S(O)-alkyl.

In the definition of alkylcarbonyl, the carbonyl carbon atom is not included in the lower and upper numeric limits for carbon atoms respectively indicated.

Preference is given to compounds of formula I, wherein $R_{17}$ is hydrogen or $C_1$–$C_8$-alkyl, and $R_{18}$ is hydrogen, $C_1$–$C_8$-alkyi, phenyl, phenyl-$C_1$–$C_8$-alkyl, whereby the phenyl rings may be substituted by fluorine, chlorine, bromine, nitro, cyano, —$OCH_3$, $C_1$–CA-alkyl or $CH_3SO_2$-; $C_1$–$C_4$-alkoxy-$C_1$–$C_8$-alkyl, $C_3$–$C_6$-alkenyl or $C_3$–$C_6$-alkinyl.

Preference is similarly given to compounds of formula I, wherein $R_1$ and $R_5$ are hydrogen.

Preference is also given to compounds of formula I, wherein A is $R_7Y$—.

Of these compounds, preference is given in particular to those in which Y is oxygen.

Preferred compounds of formula I are also those in which U is $C(R_{15})R_{16}$.

Equally preferred compounds of formula I are those in which $R_{15}$ and $R_{16}$ signify hydrogen.

Equally preferred are compounds of formula I, wherein m is 1, and V is oxygen or sulphur.

Also preferred are compounds of formula I, wherein m is 0.

Further preferred are compounds of formula I, wherein $R_1$ to $R_5$ are hydrogen, m is 1, V is oxygen, U is $C(R_{15})R_{16}$ and A is $R_7Y$—.

Of these, particular preference is given to those wherein $R_{15}$ and $R_{16}$ signify hydrogen, $R_7$ is methyl and Y is oxygen.

Important compounds of formula I are those wherein U is $C(R_{15})R_{16}$, m is 0, and $R_1$ to $R_5$ and A are defined as under formula I.

Of these, compounds that are particularly important are those in which $R_1$ to $R_5$, $R_{15}$ and $R_{16}$ are hydrogen, and A is $R_7Y$—.

Of these, the compound in which $R_7$ is methyl and Y is oxygen is quite particularly important.

The process according to the invention for the production of compounds of formula I takes place analogously to known processes, and is characterised in that a compound of formula VIIa or VIIb

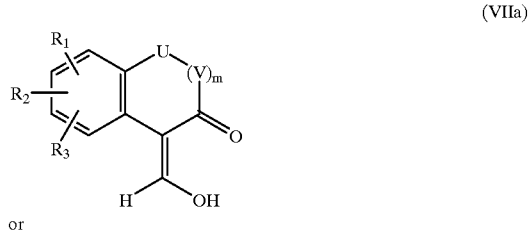

(VIIa)

or

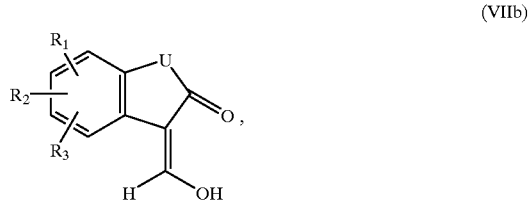

(VIIb)

wherein $R_1$ to $R_3$, U, V and m have the significances given under formula I, is allowed to react with a compound of formula X

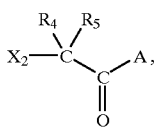
(X)

wherein $R_4$, $R_5$ and A have the significances given under formula I, and $X_2$ signifies a leaving group,
a) in the presence of a base and an organic solvent at temperatures of 0° to 100° C., or
b) in the presence of an excess of cesium fluoride in an organic solvent at temperatures of 0° to 50° C.

The process according to the invention for the production of compounds of formula VIIa

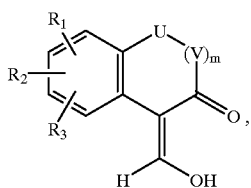
(VIIa)

wherein $R_1$ to $R_3$, U and V have the significances given under formula I and m is 1, takes place analogously to known processes, and is characterised in that a compound of formula XIa

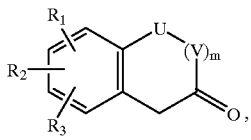
(XIa)

wherein $R_1$ to RX, U, V and m have the significances indicated, is reacted with a compound of formula VIII

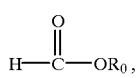
(VIII)

wherein $R_0$ is $C_1$–$C_4$-alkyl, in the presence of a base and optionally an organic solvent. The process according to the invention for the production of compounds of formula VIIb

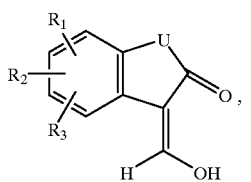
(VIIb)

wherein $R_1$ to $R_3$ and U have the significances given under formula I, and U is especially oxygen, takes place analogously to known processes, and is characterised in that a compound of formula XIb

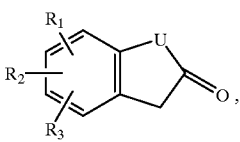
(XIb)

wherein $R_1$ to $R_3$ and U have the indicated significances, is reacted with a compound of formula IX

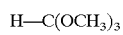
(IX)

$$H\text{—}C(OCH_3)_3$$

in the presence of an excess of acetic acid anhydride at an elevated temperature for 2 to 24 hours, to form the compound of formula VIIc

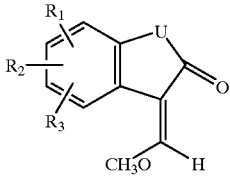
(VIIc)

and this compound undergoes enol ether cleavage with an aqueous base at 0° to 25° C., and is subsequently worked up under acidic conditions.

For the preparation of the compounds of formula I, e.g. the compounds of formula VIIa or VIIb may be reacted e.g. with an equimolar amount or an excess of reactive compound of formula X, whereby $X_2$ signifies a leaving group, for example halogen, especially chlorine or bromine,

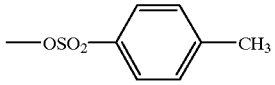

According to method a), this reaction takes place in an inert organic solvent, such as N,N-dimethylformamide (DMF), dichloromethane, tetrahydrofuran, dioxane, benzene, toluene, xylenes, dimethyl sulphoxide (DMSO) or diethylether in the presence of a base at temperatures of 0° to 100° C. Suitable bases are for example sodium or potassium hydride, butyl lithium, alcoholates e.g. sodium methylate, sodium ethylate, sodium i-propylate, sodium amylate or sodium t-butylate, trialkylamines e.g. triethylamine or tributylamine, N,N-dialkylated anilines, sodium amide ($NaNH_2$), sodium-bis-trimethylsilyl amide ($NaN(TMS)_2$), potassium-bis-trimethylsilyl amide ($KN(TMS)_2$) or lithium-bis-trimethylsilyl amide ($LiN(TMS)_2$).

According to method b), the above reaction is effected e.g. analogously to Synlett 1995, 843, in the presence of an excess (2 equivalents) of cesium fluoride in an inert organic solvent such as N,N-dimethylformamide at temperatures from 0° to 50° C., preferably 0° to 25° C. This process b) is especially suitable for reactive and towards bases unstable starting compounds.

The starting compounds of formula VIIa (m=1) and VIIb (m=0) may be produced analogously to known processes, e.g. the former in accordance with the general reaction conditions of a Claisen condensation, as described for example in Houben-Weyl, volume VII, pages 560–590; ibid, volume VlI2a, pages 492, 495, 535 and 580; and ibid, volume VI/1 d, pages 40ff. and page 275, as well as Z. Anal. Chem. 190, 243 (1962).

Accordingly, the compound of formula XIa is allowed to react with an ester of formula VIII in the presence of a base and an organic solvent such as benzene, toluene, alcohols such as methanol or ethanol, N,N-dimethylformamide or an ester, whereby the employed ester of formula VIII may itself serve as the solvent. Suitable bases for the above condensation reaction are for example sodium or potassium hydride, alcoholates such as sodium methylate or sodium ethylate, or potassium or sodium metal.

This reaction method is especially suitable for the production of compounds of formula VIIa, wherein m signifies 1.

For example, in the above manner, the new compound of formula VIIa,

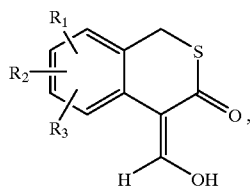

(VIIa₁)

wherein $R_1$; $R_2$ and $R_3$ have the significances given under formula I, may be prepared from the compound of formula $XIa_1$

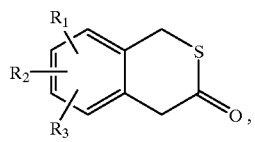

(XIa₁)

wherein $R_1$, $R_2$ and $R_3$ have the indicated significances.

The compounds of formula VIIa, are an important intermediate product for the synthesis of the compounds of formula I. The invention thus also relates to these compounds.

The starting compounds of formula VIIb may be produced e.g. analogously to WO 92/08703, Heterocycles 35, 305 (1993) or Z. Naturforsch. B, 34B, 283 (1979). The compound of formula XIb is accordingly allowed to react with the ortho-ester of formula IX in an excess of acetic acid anhydride (Ac₂O) for 2 to 24 hours at elevated temperatures, e.g. 1 00° C, to form the enol ether of formula VIIc. This may be cleaved under basic-aqueous conditions at temperatures of 0° to 25° C. Acidic-aqueous working up, for example in the presence of diluted mineral acids such as sulphuric or hydrochloricacid, yields the desired product of formula VIIb.

This method of reaction is especially suitable for the production of compounds of formula VIIb (m=0), wherein U has the significance given under formula I with the exception of $C(R_{15})R_1l$, if $R_{15}$ or $R_{16}$ signifies hydrogen, or $R_{15}$ and $R_{16}$ are hydrogen simultaneously. For these derivatives, special processes are to be considered, e.g. those indicated in Tetrahedron Lett. 32, 851 (1991) or Chem. Ber. 107, 739 (1974).

The starting compounds of formulae VII, IX, X, XIa and XIb are either known or may be produced according to disclosed processes.

For example, the production of the compound of formula XIa, is described in J. Heterocyclic Chem. 20, 811 (1983).

The production of the starting compound of formula $XIb_1$

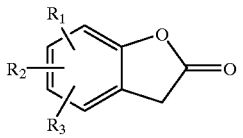

(XIb₁)

wherein $R_1$, $R_2$ and $R_3$ have the significances given under formula I, is described e.g. in FR-A-2 686 880.

The intermediate products of formula VIId

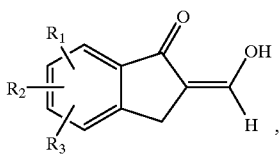

(VIId)

wherein $R_1$, $R_2$ and $R_3$ have the significances given under formula I, may be produced analogously to known processes, such as that described in J. Chem. Soc. 101, 2546 (1912), from the compounds of formula XII

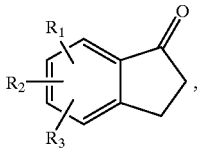

(XII)

wherein $R_1$, $R_2$ and $R_3$ have the indicated significances, e.g. in accordance with the following reaction scheme 1.

Reaction scheme 1

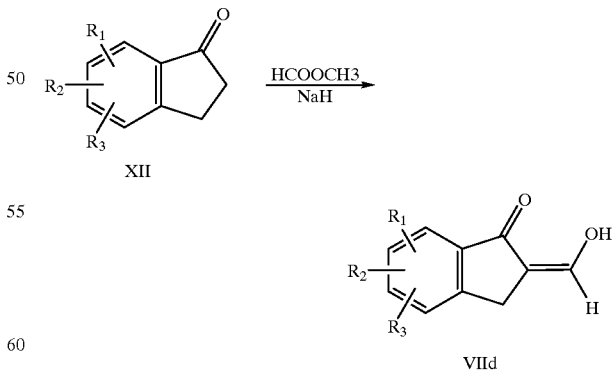

The intermediate products of formula VIIe

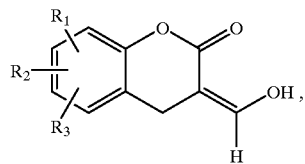
(VIIe)

wherein $R_1$, $R_2$ and $R_3$ have the significances given under formula I, may be produced analogously to known processes, such as that described in Chem. Ber. 93, 1021 (1960), from the compounds of formula XIII

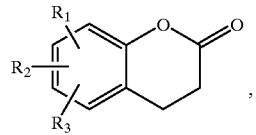
(XIII)

wherein $R_1$, $R_2$ and $R_3$ have the indicated significances.

The intermediate products of formula VIIf

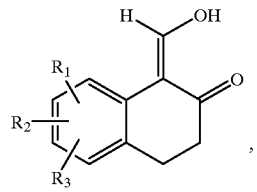
(VIIf)

wherein $R_1$, $R_2$ and $R_3$ have the significances given under formula I, may be produced analogously to known processes, such as that described in Tetrahedron Lett. 1965, 1599, from the compounds of formula $XIa_2$

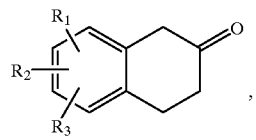
($XIa_2$)

wherein $R_1$, $R_2$ and $R_3$ have the indicated significances.

The intermediate products of formula VIIg

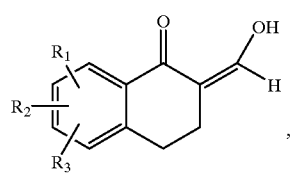
(VIIg)

wherein $R_1$, $R_2$ and $R_3$ have the significances given under formula I, may be produced analogously to known processes, such as that described in J. Org. Chem. 15, 1135 (1950), from the compounds of formula XIVa

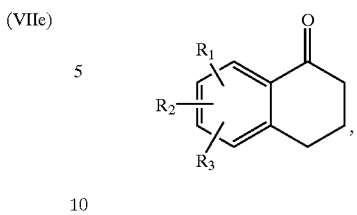
(XIVa)

wherein $R_1$, $R_2$ and $R_3$ have the indicated significances.

The intermediate products of formulae $VIIa_2$ and VIIa3

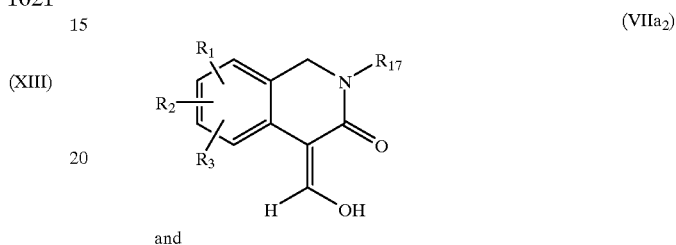
($VIIa_2$)

and

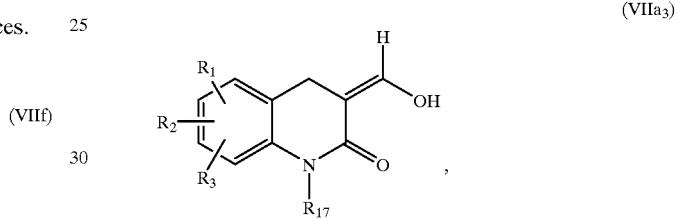
($VIIa_3$)

wherein $R_1$, $R_2$, $R_3$ and $R_{17}$ have the significances given under formula I, may be produced from the compounds of formulae XIa or XIa

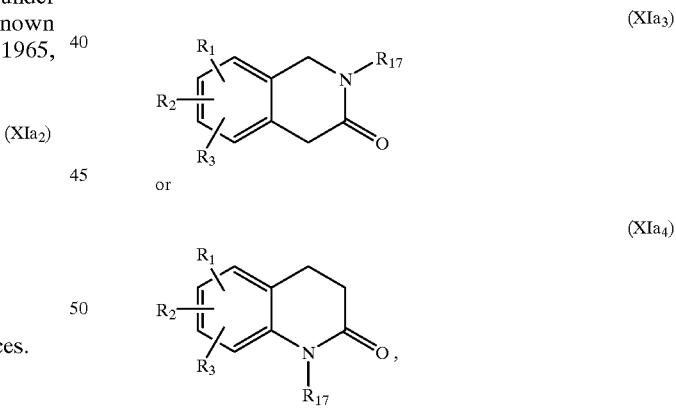
($XIa_3$)

or ($XIa_4$)

wherein $R_1$, $R_2$, $R_3$ and $R_{17}$ have the indicated significances, e.g. in accordance with the following reaction scheme 2.

Reaction scheme 2

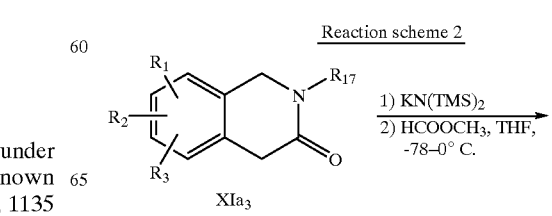

1) $KN(TMS)_2$
2) $HCOOCH_3$, THF, $-78–0°$ C.

$XIa_3$

-continued

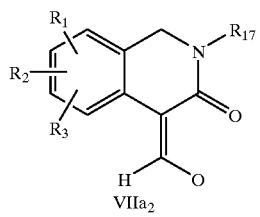

VIIa₂

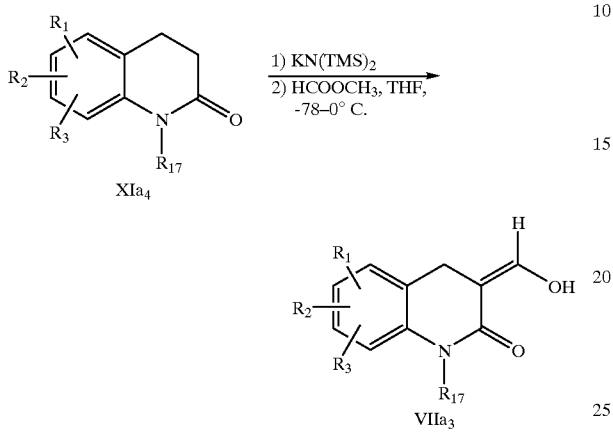

The reaction of the compounds of formulae XIa₃ and XIa₄ with the formic acid ester according to reaction scheme 2 preferably takes place in an organic solvent such as ether, for example tetrahydrofuran (THF), at temperatures of −78° C. to 0° C. and in the presence of a base such as potassium-bis-(trimethylsilyl)-amide (KN(TMS)₂).

The compounds of formulae VIIa₂ and VIIa₃ are new and represent important intermediate products in the synthesis of the compounds of formula I. The invention thus also relates to these compounds.

The educts of formula XIa₃ in reaction scheme 2 may be obtained analogously to known processes, e.g. as described in Heterocyclic Chem. 32, 73 (1995).

The educts of formula XIa₄ in reaction scheme 2 may be obtained analogously to known processes, e.g. as described in Synthesis 1987, 515.

The starting compounds of formulae XIa₂, XII, XIII and XIVa are either known or may be produced according to disclosed processes.

The following example further clarifies the invention without restricting it.

Preparation example Hi (3-oxo-isochroman-4-ylidenemethoxy)-acetic acid methyl ester 6CH (Comp. No. 01.002)

(Comp. No. 01.002)

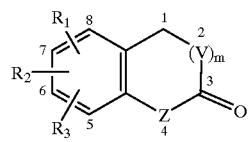

4.48 g (0.025 mols) of 3H-2-benzopyran-3-one-1,4-dihydro-4-hydroxymethylene (Z. Anal. Chem. 190, 243 (1962)) in 10 ml of DMF are added dropwise over the course of 5 minutes at −5° C. to a suspension of 1.2 g of sodium hydride (55% in oil) in 120 ml of DMF. Afterwards, 4.0 g (0.026 mols) of bromoacetic acid methyl ester are added. After removing the cooling bath, stirring continues for 1¾ hours at 25° C. The reaction mixture is subsequently poured onto a mixture of 400 ml of ice water / 50 ml of 2N aqueous hydrochloric acid /200 ml of ethyl acetate, the organic and aqueous phases are separated from one another and washed 3 times each with 100 ml of water and 100 ml of ethyl acetate. The combined organic phases are dried over sodium sulphate and concentrated. The oily residue obtained is triturated with diethylether/hexane and filtered. 5.34 g of the desired product are obtained with a m.p. of 81–82° C.

The compounds listed in the following tables may also be produced in analogous manner and according to methods illustrated in the documents cited.

TABLE 01

Compounds of formula I₀₁

(I₀₁)

| Comp. No. | R₁, R₂, R₃ | Z | V | m | Phys. data m.p. [° C.] |
|---|---|---|---|---|---|
| 01.001 | H, H, H | C=CH−O−CH₂−C(=CH)−CH | O | 1 | oil |
| 01.002 | H, H, H | C=CH−O−CH₂−COOCH₃ | O | 1 | 81–82 |

TABLE 01-continued

Compounds of formula I$_{01}$ (I$_{01}$)

[Structure: bicyclic with positions labeled R$_1$-8-1-2-(V)$_m$-3(=O)-Z-4-5-R$_3$-6-R$_2$-7]

| Comp. No. | R$_1$, R$_2$, R$_3$ | Z | V | m | Phys. data m.p. [° C.] |
|---|---|---|---|---|---|
| 01.003 | H, H, H | C=CH—O—CH$_2$—C≡CH | O | 1 | 83–86 |
| 01.004 | H, H, H | C=CH—O—CH$_2$—COOCH(CH$_3$)(CH$_2$)$_4$CH$_3$ | O | 1 | 44–46 |
| 01.005 | H, H, H | C=CH—O—CH$_2$—COOCH$_3$ | CH$_2$ | 1 | 82–84 |
| 01.006 | H, H, H | C=CH—O—CH(CH$_3$)—COOCH$_3$ | CH$_2$ | 1 | 70–72 |
| 01.007 | H, H, H | C=CH—O—CH$_2$—COOCH$_3$ | S | 1 | 94–95 |
| 01.008 | H, H, H | C=CH—O—CH$_2$—C≡CH | S | 1 | 75–76 |
| 01.009 | H, H, H | C=CH—O—CH$_2$—C≡CH | NCH$_3$ | 1 | solid |
| 01.010 | H, H, H | C=CH—O—CH$_2$—COOCH$_3$ | NCH$_3$ | 1 | 126–128 |
| 01.011 | H, H, H | C=CH—O—CH(CH$_3$)—COOCH$_3$ | NCH$_3$ | 1 | 134–137 |
| 01.012 | H, H, H | C=CH—O—CH(CH$_3$)—COOCH$_3$ | O | 1 | 104–105 |
| 01.013 | H, H, H | C=CH—O—CH(CH$_3$)—COOCH$_3$ | S | 1 | 128–129 |
| 01.014 | H, H, H | C=CH—O—CH$_2$—COOC$_2$H$_5$ | S | 1 | |
| 01.015 | H, H, H | C=CH—O—CH$_2$—COOC$_2$H$_5$ | O | 1 | |

TABLE 01-continued

Compounds of formula I$_{01}$ (I$_{01}$)

| Comp. No. | R$_1$, R$_2$, R$_3$ | Z | V | m | Phys. data m.p. [° C.] |
|---|---|---|---|---|---|
| 01.016 | H, H, H | C=CH−O−CH$_2$−COOCH$_2$−C$_6$H$_5$ | S | 1 | |
| 01.017 | H, H, H | C=CH−O−CH$_2$−COOCH$_2$−C$_6$H$_5$ | O | 1 | |
| 01.018 | H, H, H | C=CH−O−CH$_2$−CONH$_2$ | S | 1 | |
| 01.019 | H, H, H | C=CH−O−CH$_2$−CONH$_2$ | O | 1 | |
| 01.020 | H, H, H | C=CH−O−CH$_2$−CONHCH$_3$ | S | 1 | |
| 01.021 | H, H, H | C=CH−O−CH$_2$−CONHCH$_3$ | O | 1 | |
| 01.022 | H, H, H | C=CH−O−CH$_2$−CON(CH$_3$)$_2$ | S | 1 | |
| 01.023 | H, H, H | C=CH−O−CH$_2$−CON(CH$_3$)$_2$ | O | 1 | |
| 01.024 | H, H, H | C=CH−O−CH$_2$−CON(C$_2$H$_5$)$_2$ | S | 1 | |
| 01.025 | H, H, H | C=CH−O−CH$_2$−CON(C$_2$H$_5$)$_2$ | O | 1 | |
| 01.026 | H, H, H | C=CH−O−CH$_2$−CO−N(CH$_3$)(C$_6$H$_5$) | S | 1 | |
| 01.027 | H, H, H | C=CH−O−CH$_2$−CO−N(CH$_3$)(C$_6$H$_5$) | O | 1 | |

TABLE 01-continued

Compounds of formula I$_{01}$ (I$_{01}$)

| Comp. No. | R$_1$, R$_2$, R$_3$ | Z | V | m | Phys. data m.p. [° C.] |
|---|---|---|---|---|---|
| 01.028 | H, H, H | C=CH-O-CH$_2$-CO-N(CH$_3$)-cyclohexyl | S | 1 | |
| 01.029 | H, H, H | C=CH-O-CH$_2$-CO-N(CH$_3$)-cyclohexyl | O | 1 | |
| 01.030 | H, H, H | C=CH-O-CH(C$_2$H$_5$)-COOCH$_3$ | S | 1 | |
| 01.031 | H, H, H | C=CH-O-CH(C$_2$H$_5$)-COOCH$_3$ | O | 1 | |
| 01.032 | H, H, H | C=CH-O-C(CH$_3$)(CH$_3$)-COOCH$_3$ | S | 1 | |
| 01.033 | H, H, H | C=CH-O-C(CH$_3$)(CH$_3$)-COOCH$_3$ | O | 1 | |
| 01.034 | H, H, H | C=CH-O-C(cyclobutyl)-COOCH$_3$ | S | 1 | |
| 01.035 | H, H, H | C=CH-O-C(cyclohexyl)-COOCH$_3$ | O | 1 | |
| 01.036 | H, H, H | C=CH-O-C(cyclohexyl)-COOCH$_3$ | S | 1 | |

TABLE 01-continued

Compounds of formula $I_{01}$ $(I_{01})$

| Comp. No. | $R_1, R_2, R_3$ | Z | V | m | Phys. data m.p. [° C.] |
|---|---|---|---|---|---|
| 01.037 | H, H, H | C=CH—O—C(cyclohexyl)(COOCH₃) | O | 1 | |
| 01.038 | H, H, H | C=CH—O—C(cyclopentyl)(COOCH₃) | S | 1 | |
| 01.039 | H, H, H | C=CH—O—C(cyclopentyl)(COOCH₃) | O | 1 | |
| 01.040 | H, 7-CH₃, H | C=CH—O—CH₂—COOCH₃ | S | 1 | |
| 01.041 | H, 7-CH₃, H | C=CH—O—CH₂—COOCH₃ | O | 1 | |
| 01.042 | H, 6-CH₃, H | C=CH—O—CH₂—COOCH₃ | S | 1 | |
| 01.043 | H, 6-CH₃, H | C=CH—O—CH₂—COOCH₃ | O | 1 | |
| 01.044 | H, 7-OCH₃, H | C=CH—O—CH₂—COOCH₃ | S | 1 | |
| 01.045 | H, 7-OCH₃, H | C=CH—O—CH₂—COOCH₃ | O | 1 | |
| 01.046 | H, 7-Cl, H | C=CH—O—CH₂—COOCH₃ | S | 1 | |
| 01.047 | H, 7-Cl, H | C=CH—O—CH₂—COOCH₃ | O | 1 | |
| 01.048 | H, 6-Cl, H | C=CH—O—CH₂—COOCH₃ | S | 1 | |
| 01.049 | H, 6-Cl, H | C=CH—O—CH₂—COOCH₃ | O | 1 | |

TABLE 01-continued

Compounds of formula $I_{01}$ $(I_{01})$

| Comp. No. | $R_1, R_2, R_3$ | Z | V | m | Phys. data m.p. [° C.] |
|---|---|---|---|---|---|
| 01.050 | H, 8-CH$_3$, H | C=CH−O−CH$_2$−COOCH$_3$ | S | 1 | |
| 01.051 | H, 8-CH$_3$, H | C=CH−O−CH$_2$−COOCH$_3$ | O | 1 | |
| 01.052 | H, 5-CH$_3$, H | C=CH−O−CH$_2$−COOCH$_3$ | S | 1 | |
| 01.053 | H, 5-CH$_3$, H | C=CH−O−CH$_2$−COOCH$_3$ | O | 1 | |
| 01.054 | H, 8-Cl, H | C=CH−O−CH$_2$−COOCH$_3$ | S | 1 | |
| 01.055 | H, 8-Cl, H | C=CH−O−CH$_2$−COOCH$_3$ | O | 1 | |
| 01.056 | H, 5-Cl, H | C=CH−O−CH$_2$−COOCH$_3$ | S | 1 | |
| 01.057 | H, 5-Cl, H | C=CH−O−CH$_2$−COOCH$_3$ | O | 1 | |
| 01.058 | H, 6-OCH$_3$, H | C=CH−O−CH$_2$−COOCH$_3$ | S | 1 | |
| 01.059 | H, 6-OCH$_3$, H | C=CH−O−CH$_2$−COOCH$_3$ | O | 1 | |
| 01.060 | H, 8-OCH$_3$, H | C=CH−O−CH$_2$−COOCH$_3$ | S | 1 | |
| 01.061 | H, 8-OCH$_3$, H | C=CH−O−CH$_2$−COOCH$_3$ | O | 1 | |
| 01.062 | H, 5-OCH$_3$, H | C=CH−O−CH$_2$−COOCH$_3$ | S | 1 | |
| 01.063 | H, 5-OCH$_3$, H | C=CH−O−CH$_2$−COOCH$_3$ | O | 1 | |
| 01.064 | 6-OCH$_3$, 7-OCH$_3$, H | C=CH−O−CH$_2$−COOCH$_3$ | S | 1 | |

TABLE 01-continued

Compounds of formula $I_{01}$ $$(I_{01})$$

Structure: bicyclic compound with positions 1-8, R₁ at 8, R₂ at 7, R₃ at 5/6, with $(V)_m$ at position 2, Z at position 4, and C=O at position 3.

| Comp. No. | R₁, R₂, R₃ | Z | V | m | Phys. data m.p. [° C.] |
|---|---|---|---|---|---|
| 01.065 | 6-OCH₃, 7-OCH₃, H | C=CH-O-CH₂-COOCH₃ | O | 1 | |
| 01.066 | 6-CH₃, 7-CH₃, H | C=CH-O-CH₂-COOCH₃ | S | 1 | |
| 01.067 | 6-CH₃, 7-CH₃, H | C=CH-O-CH₂-COOCH₃ | O | 1 | |
| 01.068 | H, H, H | C=CH-O-CH₂-COOCH₃ | NH | 1 | |
| 01.069 | H, H, H | C=CH-O-CH(CH₃)-COOCH₃ | NH | 1 | |
| 01.070 | H, H, H | C=CH-O-CH₂-COOC₃H₇(n) | O | 1 | |
| 01.071 | H, H, H | C=CH-O-CH₂-COOC₃H₇(n) | S | 1 | |
| 01.072 | H, H, H | C=CH-O-CH₂-COOC₃H₇(i) | O | 1 | |
| 01.073 | H, H, H | C=CH-O-CH₂-COOC₃H₇(i) | S | 1 | |
| 01.074 | H, H, H | C=CH-O-CH₂-COOC₄H₉(n) | O | 1 | |
| 01.075 | H, H, H | C=CH-O-CH₂-COOC₄H₉(n) | S | 1 | |
| 01.076 | H, H, H | C=CH-O-CH₂-COOC₄H₉(sec.) | O | 1 | |
| 01.077 | H, H, H | C=CH-O-CH₂-COOC₄H₉(sec.) | S | 1 | |
| 01.078 | H, H, H | C=CH-O-CH₂-COOC₄H₉(iso) | O | 1 | |

TABLE 01-continued

Compounds of formula $I_{01}$ $(I_{01})$

| Comp. No. | $R_1, R_2, R_3$ | Z | V | m | Phys. data m.p. [° C.] |
|---|---|---|---|---|---|
| 01.079 | H, H, H | C=CH–O–CH$_2$–COOC$_4$H$_9$(iso) | S | 1 | |
| 01.080 | H, H, H | C=CH–O–CH$_2$–COOC$_4$H$_9$(tert.) | O | 1 | |
| 01.081 | H, H, H | C=CH–O–CH$_2$–COOC$_4$H$_9$(tert.) | S | 1 | |
| 01.082 | H, H, H | C=CH–O–CH$_2$–COOC$_5$H$_{11}$(n) | O | 1 | |
| 01.083 | H, H, H | C=CH–O–CH$_2$–COOC$_5$H$_{11}$(n) | S | 1 | |
| 01.084 | H, H, H | C=CH–O–CH$_2$–COOCH(CH$_3$)C$_3$H$_7$(n) | O | 1 | |
| 01.085 | H, H, H | C=CH–O–CH$_2$–COOCH(CH$_3$)C$_3$H$_7$(n) | S | 1 | |
| 01.086 | H, H, H | C=CH–O–CH$_2$–COOCH$_2$CH$_2$CH(CH$_3$)$_2$ | O | 1 | |
| 01.087 | H, H, H | C=CH–O–CH$_2$–COOCH$_2$CH$_2$CH(CH$_3$)$_2$ | S | 1 | |
| 01.088 | H, H, H | C=CH–O–CH$_2$–COOCH(C$_2$H$_5$)$_2$ | O | 1 | |
| 01.089 | H, H, H | C=CH–O–CH$_2$–COOCH(C$_2$H$_5$)$_2$ | S | 1 | |
| 01.090 | H, H, H | C=CH–O–CH$_2$–COOCH(CH$_3$)C$_4$H$_9$(n) | O | 1 | |
| 01.091 | H, H, H | C=CH–O–CH$_2$–COOCH(CH$_3$)C$_4$H$_9$(n) | S | 1 | |
| 01.092 | H, H, H | C=CH–O–CH$_2$–COOC$_6$H$_{13}$(n) | O | 1 | |
| 01.093 | H, H, H | C=CH–O–CH$_2$–COOC$_6$H$_{13}$(n) | S | 1 | |

TABLE 01-continued

Compounds of formula I$_{01}$ (I$_{01}$)

| Comp. No. | R$_1$, R$_2$, R$_3$ | Z | V | m | Phys. data m.p. [° C.] |
|---|---|---|---|---|---|
| 01.094 | H, H, H | C=CH-O-CH$_2$-COOCH(C$_2$H$_5$)C$_3$H$_7$(n) | O | 1 | |
| 01.095 | H, H, H | C=CH-O-CH$_2$-COOCH(C$_2$H$_5$)C$_3$H$_7$(n) | S | 1 | |
| 01.096 | H, H, H | C=CH-O-CH$_2$-COOC$_7$H$_{15}$(n) | O | 1 | |
| 01.097 | H, H, H | C=CH-O-CH$_2$-COOC$_7$H$_{15}$(n) | S | 1 | |
| 01.098 | H, H, H | C=CH-O-CH$_2$-COOCH(C$_2$H$_5$)C$_4$H$_9$(n) | O | 1 | |
| 01.099 | H, H, H | C=CH-O-CH$_2$-COOCH(C$_2$H$_5$)C$_4$H$_9$(n) | S | 1 | |
| 01.100 | H, H, H | C=CH-O-CH$_2$-COOC$_8$H$_{17}$(n) | O | 1 | |
| 01.101 | H, H, H | C=CH-O-CH$_2$-COOC$_8$H$_{17}$(n) | S | 1 | |
| 01.102 | H, H, H | C=CH-O-CH$_2$-COOCH(CH$_3$)C$_6$H$_{13}$(n) | O | 1 | |
| 01.103 | H, H, H | C=CH-O-CH$_2$-COOCH(CH$_3$)C$_6$H$_{13}$(n) | S | 1 | |
| 01.104 | H, H, H | C=CH-O-CH$_2$-COOCH(C$_2$H$_5$)C$_5$H$_{11}$(n) | O | 1 | |
| 01.105 | H, H, H | C=CH-O-CH$_2$-COOCH(C$_2$H$_5$)C$_5$H$_{11}$(n) | S | 1 | |
| 01.106 | H, H, H | C=CH-O-CH$_2$-COOCH$_2$CH=CH$_2$ | O | 1 | |
| 01.107 | H, H, H | C=CH-O-CH$_2$-COOCH$_2$CH=CH$_2$ | S | 1 | |

TABLE 01-continued

Compounds of formula $I_{01}$

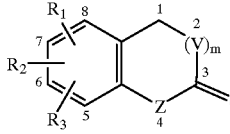

($I_{01}$)

| Comp. No. | $R_1, R_2, R_3$ | Z | V | m | Phys. data m.p. [° C.] |
|---|---|---|---|---|---|
| 01.108 | H, H, H | C=CH−O−CH₂−COOCH₂C≡CH | O | 1 | |
| 01.109 | H, H, H | C=CH−O−CH₂−COOCH₂C≡CH | S | 1 | |
| 01.110 | H, H, H | C=CH−O−CH₂−COOCH₂CF₃ | O | 1 | |
| 01.111 | H, H, H | C=CH−O−CH₂−COOCH₂CF₃ | S | 1 | |
| 01.112 | H, H, H | C=CH−O−CH₂−COOCH₂CH₂OCH₃ | O | 1 | |
| 01.113 | H, H, H | C=CH−O−CH₂−COOCH₂CH₂OCH₃ | S | 1 | |
| 01.114 | H, H, H | C=CH−O−CH₂−COO(CH₂)₃OCH₃ | O | 1 | |
| 01.115 | H, H, H | C=CH−O−CH₂−COO(CH₂)₃OCH₃ | S | 1 | |
| 01.116 | H, H, H | C=CH−O−CH₂−COO(CH₂)₂OCH₂CH=CH₂ | O | 1 | |
| 01.117 | H, H, H | C=CH−O−CH₂−COO(CH₂)₂OCH₂CH=CH₂ | S | 1 | |
| 01.118 | H, H, H | C=CH−O−CH₂−COOCH₂CH₂Cl | O | 1 | |
| 01.119 | H, H, H | C=CH−O−CH₂−COOCH₂CH₂Cl | S | 1 | |
| 01.120 | H, H, H | C=CH−O−CH₂−COOCH₂CH₂F | O | 1 | |
| 01.121 | H, H, H | C=CH−O−CH₂−COOCH₂CH₂F | S | 1 | |
| 01.122 | H, H, H | C=CH−O−CH₂−COOCH₂CH=CHCl(E) | O | 1 | |

TABLE 01-continued

Compounds of formula I$_{01}$ (I$_{01}$)

| Comp. No. | R$_1$, R$_2$, R$_3$ | Z | V | m | Phys. data m.p. [° C.] |
|---|---|---|---|---|---|
| 01.123 | H, H, H | C=CH–O–CH$_2$–COOCH$_2$CH=CHCl(E) | S | 1 | |
| 01.124 | H, H, H | C=CH–O–CH$_2$–COOCH$_2$–(4-F-C$_6$H$_4$) | O | 1 | |
| 01.125 | H, H, H | C=CH–O–CH$_2$–COOCH$_2$–(4-F-C$_6$H$_4$) | S | 1 | |
| 01.126 | H, H, H | C=CH–O–CH$_2$–COOCH$_2$CH$_2$–(4-F-C$_6$H$_4$) | O | 1 | |
| 01.127 | H, H, H | C=CH–O–CH$_2$–COOCH$_2$CH$_2$–(4-F-C$_6$H$_4$) | S | 1 | |
| 01.128 | H, H, H | C=CH–O–CH$_2$–COOCH$_2$–(4-OCH$_3$-C$_6$H$_4$) | O | 1 | |
| 01.129 | H, H, H | C=CH–O–CH$_2$–COOCH$_2$–(4-OCH$_3$-C$_6$H$_4$) | S | 1 | |
| 01.130 | H, H, H | C=CH–O–CH$_2$–COOCH$_2$–(3-CF$_3$-C$_6$H$_4$) | O | 1 | |
| 01.131 | H, H, H | C=CH–O–CH$_2$–COOCH$_2$–(3-CF$_3$-C$_6$H$_4$) | S | 1 | |
| 01.132 | H, H, H | C=CH–O–CH$_2$–COOCH$_2$–(4-Cl-C$_6$H$_4$) | O | 1 | |

TABLE 01-continued

Compounds of formula $I_{01}$ $(I_{01})$

| Comp. No. | $R_1, R_2, R_3$ | Z | V | m | Phys. data m.p. [° C.] |
|---|---|---|---|---|---|
| 01.133 | H, H, H | C=CH-O-CH$_2$-COOCH$_2$-C$_6$H$_4$-Cl | S | 1 | |
| 01.134 | H, H, H | C=CH-O-CH$_2$-COOCH$_2$-C$_6$H$_4$-CH$_3$ | O | 1 | |
| 01.135 | H, H, H | C=CH-O-CH$_2$-COOCH$_2$-C$_6$H$_4$-CH$_3$ | S | 1 | |
| 01.136 | H, H, H | C=CH-O-CH$_2$-COOCH$_2$CH=CH-C$_6$H$_5$ | O | 1 | |
| 01.137 | H, H, H | C=CH-O-CH$_2$-COOCH$_2$CH=CH-C$_6$H$_5$ | S | 1 | |
| 01.138 | H, H, H | C=CH-O-CH$_2$-COOCH$_2$C≡C-C$_6$H$_5$ | O | 1 | |
| 01.139 | H, H, H | C=CH-O-CH$_2$-COOCH$_2$C≡C-C$_6$H$_5$ | S | 1 | |
| 01.140 | H, H, H | C=CH-O-CH$_2$-COO-oxetanyl | O | 1 | |
| 01.141 | H, H, H | C=CH-O-CH$_2$-COO-oxetanyl | S | 1 | |
| 01.142 | H, H, H | C=CH-O-CH$_2$-COOCH$_2$-furyl | O | 1 | |
| 01.143 | H, H, H | C=CH-O-CH$_2$-COOCH$_2$-furyl | S | 1 | |

TABLE 01-continued

Compounds of formula I$_{01}$ (I$_{01}$)

| Comp. No. | R$_1$, R$_2$, R$_3$ | Z | V | m | Phys. data m.p. [° C.] |
|---|---|---|---|---|---|
| 01.144 | H, H, H | C=CH—O—CH$_2$—COOCH$_2$—(tetrahydrofuran-2-yl) | O | 1 | |
| 01.145 | H, H, H | C=CH—O—CH$_2$—COOCH$_2$—(tetrahydrofuran-2-yl) | S | 1 | |
| 01.146 | H, H, H | C=CH—O—CH$_2$—COOH | O | 1 | |
| 01.147 | H, H, H | C=CH—O—CH$_2$—COOH | S | 1 | |
| 01.148 | H, H, H | C=CH—O—CH$_2$—COSCH$_3$ | O | 1 | |
| 01.149 | H, H, H | C=CH—O—CH$_2$—COSCH$_3$ | S | 1 | |
| 01.150 | H, H, H | C=CH—O—CH$_2$—COOCH$_2$—C$_6$H$_4$—CF$_3$ | O | 1 | |
| 01.151 | H, H, H | C=CH—O—CH$_2$—COOCH$_2$—C$_6$H$_4$—CF$_3$ | S | 1 | |
| 01.152 | H, H, H | C=CH—O—CH$_2$—COOCH$_2$—C$_6$H$_4$—CH$_3$ | O | 1 | |
| 01.153 | H, H, H | C=CH—O—CH$_2$—COOCH$_2$—C$_6$H$_4$—CH$_3$ | S | 1 | |
| 01.154 | H, H, H | C=CH—O—CH$_2$—C(O)—N(CH(CH$_3$)$_2$)(4-F-C$_6$H$_4$) | O | 1 | |

TABLE 01-continued
Compounds of formula $I_{01}$
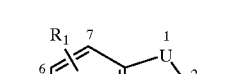
(I₀₁)
| Comp. No. | R₁, R₂, R₃ | Z | V | m | Phys. data m.p. [° C.] |
|---|---|---|---|---|---|
| 01.155 | H, H, H | C=CH—O—CH₂—C(=O)—N(CH(CH₃)₂)(4-F-C₆H₄) | S | 1 | |
| 01.156 | H, H, H | C=CH—O—CH₂—COSCH₂CH₃ | O | 1 | |
| 01.157 | H, H, H | C=CH—O—CH₂—COSCH₂CH₃ | S | 1 | |
| 01.158 | H, H, H | C=CH—O—CH(CH₃)—COSCH₃ | O | 1 | |
| 01.159 | H, H, H | C=CH—O—CH(CH₃)—COSCH₃ | S | 1 | |
| 01.160 | H, H, H | C=CH—O—C(=O)—O—CH₂CH=CHCH₃ | O | 1 | |
| 01.161 | H, H, H | C=CH—O—C(=O)—O—CH₂CH=CHCH₃ | S | 1 | |
TABLE 02
Compounds of formula $I_{02}$
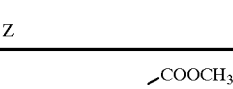
(I₀₂)
| Comp. No. | U | R₁, R₂, R₃ | Z | Phys. data m.p. [° C.] |
|---|---|---|---|---|
| 02.001 | O | H, H, H | C=CH—O—CH₂—COOCH₃ | 114–117 |

TABLE 02-continued

Compounds of formula I$_{02}$

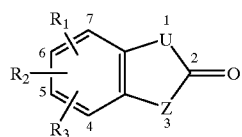

(I$_{02}$)

| Comp. No. | U | R$_1$, R$_2$, R$_3$ | Z | Phys. data m.p. [° C.] |
|---|---|---|---|---|
| 02.002 | O | H, H, H | C=CH—O—CH$_2$—C≡CH | 108–117 |
| 02.003 | O | H, 5-Cl, H | C=CH—O—CH$_2$—COOCH$_3$ | 148–150 |
| 02.004 | CH$_2$ | H, H, H | C=CH—O—CH$_2$—COOCH$_3$ | 113–117 |
| 02.005 | CH$_2$ | H, H, H | C=CH—O—CH$_2$—COO—CH$_2$—C$_6$H$_5$ | 114–116 |
| 02.006 | CH$_2$ | H, H, H | C=CH—O—CH$_2$—COOC$_2$H$_5$ | 83–85 |
| 02.007 | NH | H, 5-Cl, H | C=CH—O—CH(CH$_3$)—COOCH$_3$ | 196–197 |
| 02.008 | NH | H, 5-Cl, H | C=CH—O—CH$_2$—COOCH$_3$ | 157–159 |
| 02.009 | NH | H, H, H | C=CH—O—CH$_2$—COOCH$_3$ | 169–171 |
| 02.010 | NH | H, H, H | C=CH—O—CH(CH$_3$)—COOCH$_3$ | resin |
| 02.011 | NCH$_3$ | H, H, H | C=CH—O—CH(CH$_3$)—COOCH$_3$ | 146–147 |
| 02.012 | NCH$_3$ | H, H, H | C=CH—O—CH$_2$—COOCH$_3$ | 111–112 |
| 02.013 | S | H, H, H | C=CH—O—CH$_2$—COOCH$_3$ | |
| 02.014 | S | H, H, H | C=CH—O—CH(CH$_3$)—COOCH$_3$ | |

TABLE 02-continued

Compounds of formula $I_{02}$

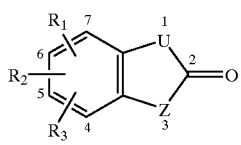

($I_{02}$)

| Comp. No. | U | $R_1, R_2, R_3$ | Z | Phys. data m.p. [° C.] |
|---|---|---|---|---|
| 02.015 | $CH_2$ | H, 6-Cl, H | C=CH—O—$CH_2$—COOCH$_3$ | |
| 02.016 | $CH_2$ | H, 6-Cl, H | C=CH—O—CH($CH_3$)—COOCH$_3$ | |
| 02.017 | $CH_2$ | H, 6-Cl, H | C=CH—O—C($CH_3$)$_2$—COOCH$_3$ | |
| 02.018 | $CH_2$ | H, 6-OCH$_3$, H | C=CH—O—$CH_2$—COOCH$_3$ | |
| 02.019 | $CH_2$ | H, 6-OCH$_3$, H | C=CH—O—C($CH_3$)$_2$—COOCH$_3$ | |
| 02.020 | $CH_2$ | 6-CH$_3$, H, H | C=CH—O—$CH_2$—COOCH$_3$ | |
| 02.021 | $CH_2$ | 6-CH$_3$, H, H | C=CH—O—CH($CH_3$)—COOCH$_3$ | |
| 02.022 | $CH_2$ | H, 5-Cl, H | C=CH—O—$CH_2$—COOCH$_3$ | |
| 02.023 | $CH_2$ | 5-OCH$_3$, H, H | C=CH—O—$CH_2$—COOCH$_3$ | |
| 02.024 | $CH_2$ | 5-CH$_3$, H, H | C=CH—O—$CH_2$—COOCH$_3$ | |
| 02.025 | $CH_2$ | 5-OCH$_3$, 6-OCH$_3$, H | C=CH—O—$CH_2$—COOCH$_3$ | |
| 02.026 | $CH_2$ | 5-CH$_3$, 6-CH$_3$, H | C=CH—O—$CH_2$—COOCH$_3$ | |
| 02.027 | $CH_2$ | 7-CH$_3$, H, H | C=CH—O—$CH_2$—COOCH$_3$ | |

TABLE 02-continued

Compounds of formula I$_{02}$ (I$_{02}$)

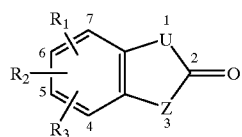

| Comp. No. | U | R$_1$, R$_2$, R$_3$ | Z | Phys. data m.p. [° C.] |
|---|---|---|---|---|
| 02.028 | CH$_2$ | 4-CH$_3$, H, H | C=CH–O–CH$_2$–COOCH$_3$ | |

TABLE 03

Compounds of formula I$_{03}$ (I$_{03}$)

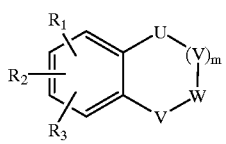

| Comp. No. | U | V | m | W | Z | R$_1$, R$_2$, R$_3$ | Phys. data m.p. [° C.] |
|---|---|---|---|---|---|---|---|
| 03.001 | O | C=O | 1 | C=CH–O–CH$_2$–C≡CH | CH$_2$ | H, H, H | waxy |
| 03.002 | O | C=O | 1 | C=CH–O–CH$_2$–COOCH$_3$ | CH$_2$ | H, H, H | 71–73 |
| 03.003 | CH$_2$ | C=O | 1 | C=CH–O–CH(CH$_3$)–COOCH$_3$ | CH$_2$ | H, H, H | 123–125 |
| 03.004 | CH$_2$ | C=O | 1 | C=CH–O–CH$_2$–COOCH$_3$ | CH$_2$ | H, H, H | 98–100 |
| 03.005 | CH$_2$ | CH$_2$ | 1 | C=CH–O–CH$_2$–COOCH$_3$ | C=O | H, H, H | 97–98 |
| 03.006 | CH$_2$ | CH$_2$ | 1 | C=CH–O–CH(CH$_3$)–COOCH$_3$ | C=O | H, H, H | 55–58 |
| 03.007 | NCH$_3$ | C=O | 1 | C=CH–O–CH$_2$–COOCH$_3$ | CH$_2$ | H, H, H | waxy |
| 03.008 | CHCH$_3$ | O | 1 | C=O | C=CH–O–CH$_2$–COOCH$_3$ | H, H, H | |
| 03.009 | CHCH$_3$ | S | 1 | C=O | C=CH–O–CH$_2$–COOCH$_3$ | H, H, H | |

TABLE 03-continued

Compounds of formula $I_{03}$ $(I_{03})$

| Comp. No. | U | V | m | W | Z | $R_1, R_2, R_3$ | Phys. data m.p. [° C.] |
|---|---|---|---|---|---|---|---|
| 03.010 | $C(CH_3)_2$ | O | 1 | C=O | C=CH–O–CH$_2$–COOCH$_3$ | H, H, H | |
| 03.011 | $C(CH_3)_2$ | S | 1 | C=O | C=CH–O–CH$_2$–COOCH$_3$ | H, H, H | |

TABLE 04

Compounds of formula $I_{04}$ $(I_{04})$

| Comp. No. | $R_1, R_2, R_3$ | W | Phys. data m.p. [° C.] |
|---|---|---|---|
| 04.001 | H, 6-Cl, H | C=CH–O–CH$_2$–COOCH$_3$ | 144–146 |
| 04.002 | H, 6-Cl, H | C=CH–O–CH(CH$_3$)–COOCH$_3$ | 98–100 |
| 04.003 | H, H, H | C=CH–O–CH$_2$–C≡CH | 119–121 |
| 04.004 | H, H, H | C=CH–O–CH(CH$_3$)–COOCH$_3$ | 104–106 |
| 04.005 | H, H, H | C=CH–O–CH$_2$–COOCH$_3$ | 114–116 |

The compounds of formula I according to the invention may be used as antidotes in herbicidal compositions.

When using herbicides, the cultivated plants may also be damaged to a considerable extent e.g. depending on the dosage of herbicide and the type of application, the plant being cultivated, the constitution of the soil and the climatic conditions, such as duration of light, temperature and amount of rainfall.

In order to counteract this and similar problems, already many substances have been proposed as antidotes. These are capable of antagonizing the damaging activity of the herbicide on the cultivated plant, that is, protecting the cultivated plant therefrom, whereby however the herbicide activity on the weeds to be controlled is practically unimpaired. As a result, it has been shown that the proposed antidotes often have very specific activity both in regard of the cultivated plants and in regard of the herbicide and partly also depending on the type of application. This means that a certain antidote is often only suitable for a certain cultivated plant and a particular class of herbicide substance or a certain herbicide.

It has now been found that the compounds of formula I according to the invention are suitable for protecting cultivated plants from the phytotoxic activity of certain classes of aryloxy-phenoxypropionic acid ester, sulphonylurea, sulphonamide, 3-hydroxy-4-aryl-5-oxo-pyrazoline and chloracetanilide herbicides and the herbicide isoxaflutol (EXP-30953).

Thus, in accordance with the invention, a herbicidal composition having selective herbicide activity is also proposed, which is characterised in that, in addition to the usual inert formulation assistants such as carriers, solvents and wetting agents, it contains as the active ingredient a mixture of a) a herbicidally active amount of a herbicide of formulae II to VII

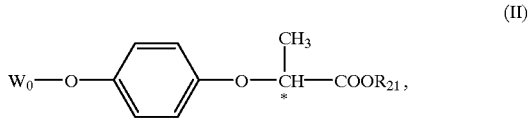

(II)

wherein $R_{21}$ signifies $C_1$–$C_4$-alkyl, propargyl or the group -$CH_2CH_2$-O-N=$C(CH_3)_2$; and $W_o$ signifies the groups

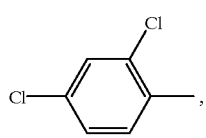

($W_1$)

-continued (W₂) 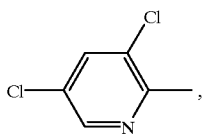

(W₃) 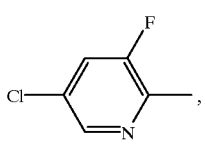

(W₄) 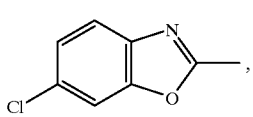

(W₅) 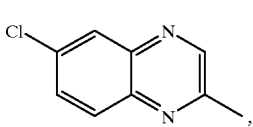

(W₆) 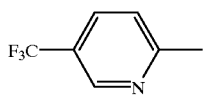

or (W₇) 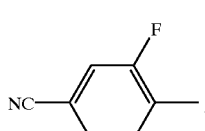
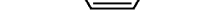

and in particular the (R)-enantiomers (*) of these compounds; or of formula III (III) 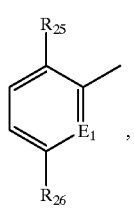

wherein $Z_o$ signifies a group (Z₁) 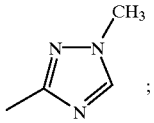

(Z₂) 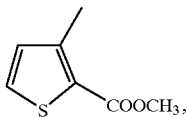

(Z₃) 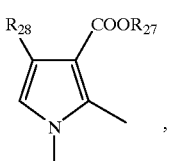

(Z₄) 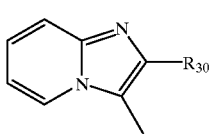

or (Z₅) $CH_3—SO_2—$ ;

$R_{22}$ signifies hydrogen or $CH_3$;

$R_{23}$ signifies $CH_3$, $—OCH_3$, $—OCHF_2$, Cl, $—N(CH_3)_2$, $—NHCH_3$ or $CF_3$;

$R_{24}$ signifies $CH_3$, $—OCH_3$, $—OCHF_2$, $—OCH_2CF_3$ or $—OC_2H_5$;

$R_{25}$ signifies $—OC_2H_5$, $—OCH_2CH_2Cl$, $—COOCH_3$, $-COOC_2H_5$

$—O—CH_2CH_2—O—CH_3$, Cl, $—CON(CH_3)_2$, $—SO_2C_2H_5$, $CF_3$, $—OCHF_2$,

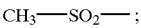

$—N(CH_3)SO_2CH_3$ or $—N(CH_3)COCH_3$;

$R_{26}$ signifies hydrogen, $CH_3$, $—OCH_3$, $CF_3$, $CHF_2$ or $—OCHF_2$;

$R_{27}$ signifies $CH_3$, $C_2H_5$ or the group

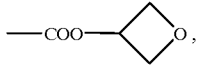

$R_{28}$ signifies hydrogen or chlorine;

$R_{29}$ signifies $CH_3$ or the group

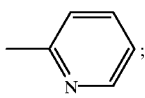;

$R^{30}$ signifies —$SO_2C_2H_5$ or chlorine;
E signifies nitrogen or methine;
$E_1$ signifies nitrogen, methine or C—$CH_3$;
$E_2$ signifies nitrogen or methine;
B signifies oxygen, —NH— or methylene; and
$n_1$ signifies 0 or 1,
as well as agronomically compatible salts of these compounds; or of formula IV

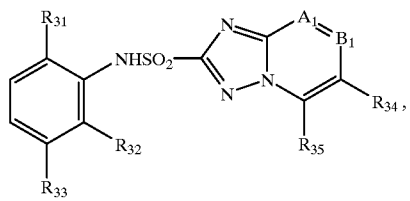 (IV)

wherein
$R_{31}$ is fluorine or chlorine;
$R_{32}$ is fluorine, chlorine or —$COOCH_3$;
$R_{33}$ is hydrogen or methyl;
$R_{34}$ is hydrogen or fluorine;
$R_{35}$ is hydrogen or methoxy;
$A_1$ is nitrogen or C—$OC_2H_5$; and
$B_1$ is nitrogen, C—$CH_3$ or C—$OCH_3$; or of formula V

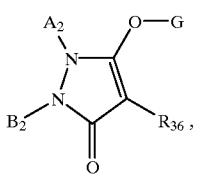 (V)

wherein
$R_{36}$ signifies the group

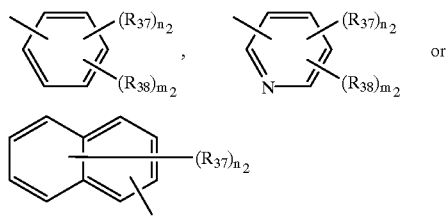

the substituents $R_3 1$, independently of one another, signify halogen, nitro, cyano, $C_1$–$C_4$-alkyl, $C_1$–$C_4$-halogen-alkyl, $C_1$–$C_4$-alkoxy, $C_1$–$C_4$-halogen-alkoxy, $C_3$–$C_6$-alkenyloxy, $C_1$–$C_4$-alkoxy-$C_2$–$C_4$-alkoxy, $C_3$–$C_6$-alkinyloxy, $C_1$–$C_4$-alkylcarbonyl, $C_1$–$C_4$-alkoxycarbonyl, $C_1$–$C_4$-alkylthio, $C_1$–$C_4$-alkylsulphinyl, $C_1$–$C_4$-sulphonyl, amino, $C_1$–$C_4$-alkylamino or di-$C_1$–$C_4$-alkylamino;

$R_{38}$ signifies the group

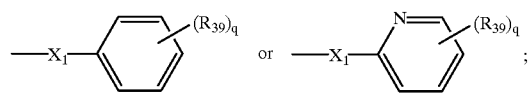;

$n_2$ signifies 0, 1, 2, 3 or 4;
$m_2$ signifies 0 or 1, whereby the sum of $m_2$ and $n_2$ is 0, 1, 2, 3 or 4;
q signifies 0, 1, 2 or 3;
$X_1$ is oxygen, sulphur, —$CH_2$- or —N($R_{40}$)—; the substituents RF, independently of one another, are $C_1$–$C_4$-alkyl, halogen, $C_1$–$C_4$-halogen-alkyl, $C_1$–$C_4$-alkoxy, $C_1$–$C_4$-halogen-alkoxy, nitro, cyano, $C_1$–$C_4$-alkoxycarbonyl, amino, $C_1$–$C_4$-alkylamino or di-$C_1$–$C_4$-alkylamino;
$R_{40}$ signifies hydrogen, $C_1$–$C_4$-alkyl, formyl or $C_1$–$C_4$-alkylcarbonyl;
$A_2$ and $B_2$, independently of one another, signify hydrogen, alkyl, alkenyl, alkinyl, alkoxyalkyl, alkylthioalkyl or cycloalkyl, or optionally substituted aryl; or $A_2$ and $B_2$ together form the bivalent radical of a saturated or unsaturated and optionally substituted mono-, bi-, tri- or polycyclic system;
G signifies hydrogen or the groups —CO—$R_{41}$ (a),

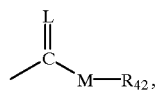 (b)

—$SO_2$—$R_{43}$ (c),

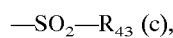 (d)

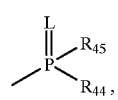 (e)

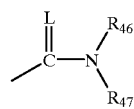

or $M_1$ (f)
L and M, independently of one another, are oxygen or sulphur;
$R_{41}$ is halogen-alkyl, alkenyl, alkoxyalkyl, alkylthioalkyl, polyalkoxyalkyl or cycloalkyl, which may contain hetero atoms, optionally substituted phenyl, optionally substituted phenylalkyl, substituted heteroaryl, substituted phenoxyalkyl or substituted heteroaryloxyalkyl;
$R_{42}$ is halogen-alkyl, alkenyl, alkoxyalkyl or polyalkoxyalkyl, or optionally substituted phenyl or benzyl;
$R_{43}$, $R_{44}$ and $R_{45}$, independently of one another, are alkyl, halogen-alkyl, alkoxy, alkylamino, dialkylamino, alkylthio, alkenylthio, alkinylthio or cycloalkylthio, or optionally substituted phenyl, phenoxy or phenylthio;
$R_{46}$ and $R_{47}$, independently of one another, are hydrogen, alkyl, halogen-alkyl, alkenyl, alkoxy or alkoxyalkyl, optionally substituted phenyl or benzyl; or $R_{46}$ and $R_{47}$ together form an alkylene radical, which may optionally contain oxygen as a hetero atom; and $M_1$ signifies a metal ion equivalent or an ammonium ion, as well as salts and diastereoisomers of the compounds of formula V; or of formula VI (VI)

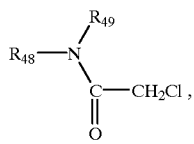

wherein $R_{48}$ signifies a group

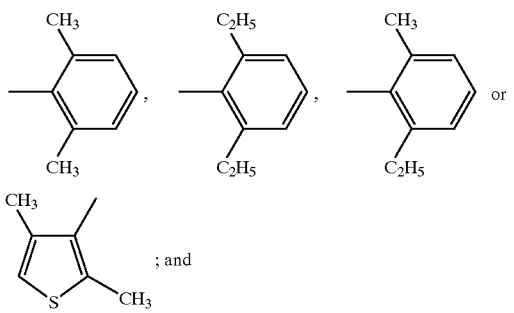

$R_{49}$ signifies a group $-CH(CH_3)CH_2OCH_3$, $-CH_2OCH_3$ or $-CH_2OC_2H_5$; or of formula VII

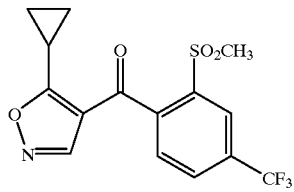

(VII, lsoxaflutol EXP-30953); and b) an amount of an antidote of formula I (I)

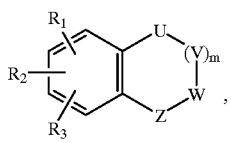

having herbicide-antagonistic activity, wherein $R_1$ is hydrogen, $C_1-C_4$-alkyl, $C_1-C_4$-alkyl substituted by $C_1-C_4$-alkyl-X- or $C_1-C_4$-halogen-alkyl-X-, $C_1-C_4$-halogen-alkyl, nitro, cyano, $-COOR_8$, $-NR_9R_{10}$, $-SO_2NR_{11}R_{12}$ or $-CONR_{13}R_{14}$;

$R_2$ is hydrogen, halogen, $C_1-C_4$-alkyl, trifluoromethyl, $C_1-C_4$-alkoxy or $C_1-C_4$-halogen-alkoxy;

$R_3$ is hydrogen, halogen or $C_1-C_4$-Alkyl;

U, V, W and Z independently of one another, are oxygen, sulphur, $C(R_{15})R_{16}$, carbonyl, $NR_{17}$ or a group

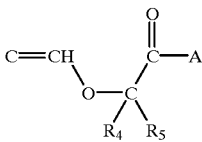

with the provisos that a) at least one of the ring members U. V, W or Z is carbo a ring member which is adjacent to this orthese ing members signifies the group

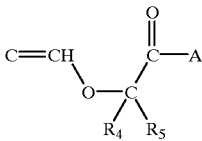

whereby this group only appears once; and b) two adjacent ring members U and V, V and W and W and Z may not simultaneously signify oxygen;

$R_4$ and $R_5$, independently of one another, signify hydrogen or $C_1-C_8$-alkyl; or $R_4$ and R together form a $C_2-C_6$-alkylene group;

A is RrY— or $-NR_{18}R_{19}$;

X is oxygen or $-S(O)_p$;

Y is oxygen or sulphur;

$R_7$ is hydrogen, $C_1-C_8$-alkyl, $C_1-C_8$-halogen-alkYl, $C_1-C_4$-alkoxy-$C_1-C_8$-alkyl, $C_3-C_6$-alkenyloxy-$C_1-C_8$-alkyl or phenyl-$C_1-C_8$-alkyl, whereby the phenyl ring may be substituted by halogen, $C_1-C_4$-alkyl, trifluormethyl, methoxy or methyl—$S(O)_p$-; $C_3-C_6$-alkenyl, $C_3-C_6$-halogen-alkenyl, phenyl-$C_3-C_8$-alkenyl, $C_3-C_8$-alkinyl, phenyl-$C_3-C_6$-alkinyl, oxetanyl, furfuryl or tetrahydrofurfuryl;

$R_8$ is hydrogen or $C_1-C_4$-alkyl;

$R_9$ is hydrogen, $C_1-C_4$-alkyl or $C_1-C_4$-alkylcarbonyl;

$R_{10}$ is hydrogen or $C_1-C_4$-alkyl; or $R_9$ and $R_{10}$ together form a $C_4$- or $C_8$-alkylene group;

$R_{11}$, $R_{12}$, $R_{13}$ and $R_{14}$ independently of one another, are hydrogen or $C_1-C_4$-alkyl; or $R_{11}$ together with $R_{12}$ or $R_1$t together with $R_{14}$ independently of one another, are $C_4$- or $C_5$-alkylene, whereby one carbon atom may be replaced by oxygen or sulphur, or one or two carbon atoms may be replaced by $-NR_{15}-$;

$R_{15}$ and $R_{16}$ independently of one another, are hydrogen or $C_1-C_8$-alkyl; or $R_{15}$ and $R_{18}$ together are $C_2-C_6$-alkylene;

$R_{17}$ is hydrogen, $C_1-C_8$-alkyl, optionally substituted phenyl or benzyl optionally substituted on the phenyl ring;

$R_{18}$ is hydrogen, $C_1-C_8$-alkyl, phenyl, phenyl-$C_1-C_8$-alkyl, whereby the phenyl ring may be substituted by fluorine, chlorine, bromine, nitro, cyano, $-OCH_3$, $C_1-C_4$-alkyl or $CH_3SO_2-$; $C_1-C_4$-alkoxy-$C_1-C_8$-alkyl, $C_3-C_6$-alkenyl, $C_3-C_8$-alkinyl or $C_3-C_6$-cycloalkyl;

$R_{19}$ is hydrogen, $C_1-C_8$-alkyl, $C_3-C_6$-alkenyl or $C_3-C_6$-alkinyl; or $R_{18}$ and $R_{19}$ together are $C_4$- or $C_5$-alkylene, whereby one carbon atom may be replaced by oxygen or sulphur, or one or two carbon atoms may be replaced by $-NR_{20}-$;

$R_{20}$ is hydrogen or $C_1-C_4$-alkyl;

m is 0 or 1; and p signifies 0, 1 or 2, as well as agronomically compatible salts and stereoisomers of these compounds.

Preferred compositions according to the present invention contain clodinafop, quizalafop, propaquizafop, fenoxaprop, fluazifop and cyhalofop as the herbicides of formula II.

Preferred compositions according to the present invention contain tribenuron, metsulfuron, primisulfuron, ethametsulfuron, sulfometuron, chlorimuron, oxasulfuron [presented on the occasion of the Brighton Crop Protection Conference—Weeds—1995 (Plenary Session 2, Nov. 21, 1995, Proceedings Vol. 2, page 79)), triasulfuron, cinosulfuron, triflusulfuron, bensulfuron, ethoxysulfuron, sulfazuron, nicosulfuron, rimsulfuron, flupyrsulfuron, thifensulfuron, clopyrazosulfuron (NC-319), pyrazosulfuron (NC-31 1), sulfosulfuron (NC-330, known from U.S. Pat. No. 4 895 590), azimsulfuron und amidosulfuron as the herbicides of formula 111, well as the compounds of formulae IIIa to IIId (IIIa)

known from EP-B-0 496 701;

(IIIb)

known from US-A-5-009 699;

(IIIc)

MON-375 ), known from (IIId)

known from DE-OS-4 128 441

Preferred compositions according to the present invention contain flumetsulam, metosulam und cloransulam as herbicides of foromua IV.

Preferred compositions according to the present invention contain the herbicides of formula V (V)

wherein $R_{36}$ is mesitylenyl or $A_2$ and $B_2$ are methyl; or $A_2$ and $B_2$ together form a -$(CH_2)_4$- group; and G signifies hydrogen or —$COC(CH_3)_3$.

Of these, the herbicides of formula V according to table 1 are preferred in particular.

TABLE 1

Especially preferred herbicides of formula V (V)

| Comp. No. | $A_2$ | $B_2$ | $R_{36}$ | G |
|---|---|---|---|---|
| 1.1 | —$(CH_2)_4$— | | $CH_3$ (mesitylenyl) | H |

TABLE 1-continued

Especially preferred herbicides of formula V (V)

[Structure of formula V with A₂, B₂, N-N, O-G, R₃₆, O]

| Comp. No. | A₂ | B₂ | R₃₆ | G |
|---|---|---|---|---|
| 1.2 | —(CH₂)₄— | | $C_2H_5$ | H |
| | | | [phenyl ring with three $C_2H_5$ groups] | |
| 1.3 | $CH_3$ | $CH_3$ | [phenyl ring with three $CH_3$ groups] | —C(O)C(CH₃)₃ |

Preferred compositions according to the present invention contain metolachlor, alachlor, acetochlor, dimethenamide and in particular aRS,1'S(−)N-(1'-methyl-2'-methoxyethyl)-N-chloracetyl-2-ethyl-6-methylaniline, known from U.S. Pat. No. 5 002 606, as herbicides of formula VI.

The compounds described by common names e.g. under formula It, such as ctodinafop, under formula III such as primisulfuron, under formula IV such as flumetsulam, under formula VI such as metolachlor and under formula VII (isoxaflutol) are known in part as commercial products or may be referred to for example in current agrochemical handbooks, e.g. 'The Pesticide Manual', The British Crop Protection Council, London; or 'The Agrochemicals Handbook', The Royal Society of Chemistry.

The compounds of formula V are known from international patent application No. PCT/EP 95103935.

Preferred compositions according to the present invention are characterised in that they contain as the compound of formula I (3-oxo-isochroman-4-ylidenemethoxy)-acetic acid methyl ester (compound no. 01.002) in combination with clodinafop, primisulfuron, chlorimuron or in combination with the compound of formula (IIIa)

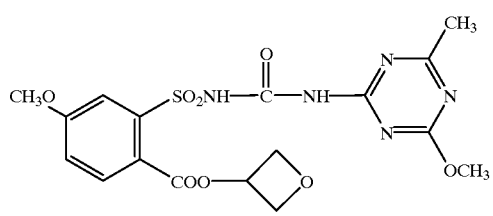

or (Comp. No. 1.3)

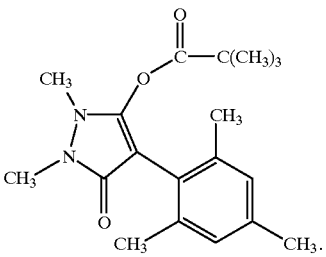

Equally preferred compositions according to the present invention are characterised in that they contain as the compound of formula I (2-oxo-indan-1-ylidenemethoxy)-acetic acid methyl ester (compound no. 02.004) in combination with clodinafop, primisulfuron, chlorimuron or in combination with the compound of formula (IIIa)

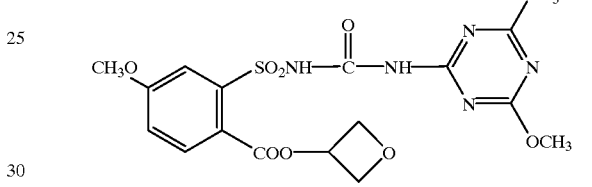

or (Comp. No. 1.3)

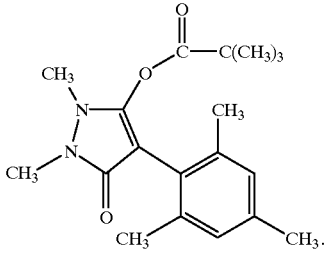

Compositions according to the present invention which are also preferred are characterised in that they contain as the compound of formula I (3-oxo-isochrom-4-ylidenemethoxy)-acetic acid methyl ester (comp. no. 01.002), (2-oxo-indan-1-ylidenemethoxy)- acetic acid methyl ester (comp. no. 02.004) or (3-oxo-isothiochroman-4-ylidenemethoxy)- acetic acid methyl ester (comp. no. 01.007) and as the active ingredient of formula II clodinafop, as active ingredients of formula III primisulfuron, chlorimuron or the compound of formula (IIIa)

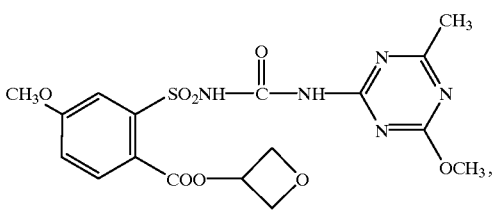

as active ingredient of formula V the compound of formula (Comp. No. 1.3)

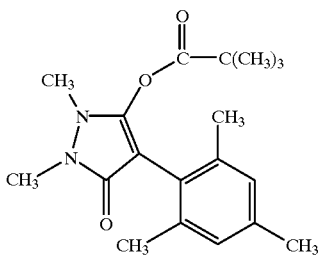

and as active ingredient the compound of formula VII (VII)

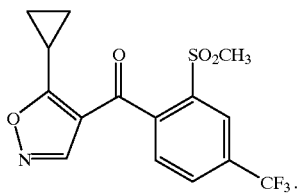

The invention also relates to a process for the selective control of weeds in useful plant cultivations, which comprises treating the useful plants, their seeds or cuttings or their cultivation area simultaneously or separately with a herbicidally active amount of a herbicide of formulae II to VI and a herbicide-antagonistically active amount of the antidote of formula I.

The cultivated plants that may be protected by the antidotes of formula I against the damaging action of the above-mentioned herbicides are in particular maize, cereals, soybeans and eice. The cultivations are understood to be also those which have been made tolerant towards herbicides or classes of herbicide by conventional growing methods or genetic engineering methods.

The weeds to be controlled may be both monocotyledonous and dicotyledonous weeds, for example *Stellaria, Nasturtium, Agrostis, Digitaria, Avena, Setaria, Sinapis, Lolium, Solanum, Phaseolus, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Viola* and *Veronica*.

The cultivation areas include the soil on which the cultivated plants are already growing or on which seed of these cultivated plants has already been sown, and also the soil on which these cultivated plants are intended to be raised.

Depending on the purpose of application, an antidote of formula I may be employed for the pre-treatment of the seed grain of the culvitated plant (dressing of the seed or cuttings) or may be added to the soil before or after sowing. However, it may also be applied on its own or together with the herbicide after emergence of the plants. Therefore, treatment of the plants or the seed grain with the antidote may basically take place independently of the time of application of the herbicide. However, treatment of the plant may also be undertaken by means of simultaneous application of herbicide and antidote (e.g. as a tank mixture).

The application rate of antidote to herbicide to be employed depends to a great extent on the type of application. For field treatment, which is effected either using a tank mixture with a combination of antidote and herbicide or by means of separate application of antidote and herbicide, a ratio of herbicide to antidote of 1:100 to 100:1, preferably 1:20 to 20:1 is normal.

As a rule, for field treatment, 0.001 to 5.0 kg antidote/ha, preferably 0.001 to 0.5 kg antidote/ha is applied.

The amounts of herbicide applied are usually between 0.001 and 2 kg/ha, but preferably between 0.005 and 1 kg/ha.

The compositions according to the invention are suitable for all application methods that are customary in agriculture, such as pre-emergent application, post-emergent application and seed dressing.

For seed dressing, in general 0.001 to 10 g of antidote/kg seeds, preferably 0.05 to 2 g antidote/kg seeds is applied. If the antidote is applied in liquid form shortly prior to sowing whereby the seed swells, antidote solutions which contain the active ingredient in a concentration of 1 to 10,000, preferably 100 to 1000 ppm are suitably used.

In order to apply them, the antidotes of formula I or combinations of these antidotes with the herbicides of formulae II to VI are conveniently processed with the assistants which are customary in formulation technology into formulations, e.g. into emulsion concentrates, coatable pastes, directly sprayable or dilutable solutions, diluted emulsions, wettable powders, soluble powders, dusts, granulates or micro-capsules. The formulations are produced in a manner known per se, e.g. by intimately mixing and/or grinding the active ingredients with liquid or solid formulating assistants such as solvents or solid carriers. In addition, surface-active compounds (surfactants) may be used when producing the formulations.

The solvents in question may be: aromatic hydrocarbons, preferably fractions $C_8$ to $C_{12}$, such as xylene mixtures or substituted naphthalenes, phthalic acid esters such as dibutyl or dioctyl phthalate, aliphatic hydrocarbons such as cyclohexane or paraffins, alcohols and glycols, as well as the ethers and esters thereof, such as ethanol, ethylene glycol, ethylene glycol monomethyl- or -ethyl-ether, ketones such as cyclohexanone, strongly polar solvents such as N-methyl-2-pyrrolidone, dimethyl suiphoxide or N,N-dimethylformamide, as well as optionally epoxidated vegetable oils such as epoxidated coconut oil or soybean oil; or water.

The solid carriers employed e.g. for dusts and dispersible powders are normally natural mineral powders, such as calcite, talc, kaolin, montmorillonite or attapulgite. To improve the physical properties of the formulation, highly disperse silicic acid or highly disperse absorbent polymerisates may also be added. The granular, adsorptive granulate carriers employed may be porous types such as pumice, brick fragments, sepiolite or bentonite, and the nonabsorbent carrier materials are e.g. calcite or sand. Moreover, a number of pregranulated materials of inorganic or organic nature may also be used, especially dolomite or pulverized plant residue.

Depending on the type of active ingredients of formulae If to VI to be formulated, the surface-active compounds may be non-ionic, cationic and/or anionic surfactants and surfactant mixtures having good emulsifying, dispersing and wetting properties.

Appropriate anionic surfactants may be both so-called water-soluble soaps and water-soluble synthetic surface-active compounds.

Soaps which may be mentioned are the alkali salts, alkaline earth salts or optionally substituted ammonium salts of higher fatty acids ($C_{10}$–$C_{22}$), e.g. the Na or K salts of oleic or stearic acid, or of natural fatty acid mixtures, which may be obtained e.g. from coconut oil or tallow oil. Furthermore, the fatty acid methyl-taurine salts may also be mentioned.

More frequently however, so-called synthetic surfactants are used, especially fatty alcohol sulphonates, fatty alcohol sulphates, sulphonated benzimidazole derivatives or alkylaryl sulphonates.

The fatty alcohol sulphonates or sulphates are normally present as alkali salts, alkaline earth salts or optionally substituted ammonium salts and have an alkyl radical with 8 to 22 C-atoms, whereby alkyl also includes the alkyl moiety of acyl radicals, e.g. the Na or Ca salt of lignin sulphonic acid, of dodecylsulphuric acid ester or of a fatty alcohol sulphate mixture produced from natural fatty acids. This also includes the salts of sulphuric acid esters and sulphonic acids of fatty alcohol/ethylene oxide adducts. The sulphonated benzimidazole derivatives preferably contain 2 sulphonic acid groups and one fatty acid radical with 8–22 carbon atoms. Alkylaryl sulphonates are e.g. the Na, Ca or triethanolamine salts of dodecylbenzenesulphonic acid, of dibutyinaphthalene-sulphonic acid or of a naphthalene-sulphonic acid I formaldehyde condensation product.

The corresponding phosphates such as the salts of the phosphoric acid ester of a p-nonyl-phenol-(4–14)-ethylene oxide adduct or phospholipids may also be considered.

The non-ionic surfactants may be primarily polyglycol ether derivatives of aliphatic or cycio-aliphatic alcohols, saturated or unsaturated fatty acids and alkylphenols, which may contain 3 to 30 glycol ether groups and 8 to 20 carbon atoms in the (aliphatic) hydrocarbon radical and 6 to 18 carbon atoms in the alkyl radical of the alkylphenols.

Further appropriate non-ionic surfactants are the water-soluble polyethylene oxide adducts to polypropylene glycol, ethylenediamino-polypropylene glycol and alkyl-polypropylene glycol, containing 20 to 250 ethylene glycol ether groups and 10 to 100 propylene glycol ether groups, with 1 to 10 carbon atoms in the alkyl chain. The said compounds normally contain 1 to 5 ethylene glycol units per propylene glycol unit.

Examples of non-ionic surfactants which may be mentioned are nonylphenol polyethoxy ethanols, castor oil polyglycol ether, polypropylene-polyethylene oxide adducts, tributyl-phenoxy-polyethoxy ethanol, polyethylene glycol and octylphenoxy-polyethoxy ethanol.

Fatty acid esters of polyoxyethylene sorbitan, such as polyoxyethylene sorbitan trioleate, may also be considered.

The cationic surfactants in question are in particular quaternary ammonium salts, which contain as the N-substituents at least one alkyl radical with 8 to 22 C-atoms and as further substituents low, optionally halogenated alkyl, benzyl or low hydroxyalkyl radicals. The salts are preferably present as halides, methyl sulphates or ethyl sulphates, e.g. stearyl trimethylammonium chloride or benzyl-di-(2-chloroethyl)-ethylammonium bromide.

The surfactants which are customary in formulation techniques and which may also be used in the compositions according to the invention are described inter alia in "Mc Cutcheon's Detergents and Emulsifiers Annual" MC Publishing Corp., Ridgewood N.J., 1981, Stache, H., "Tensid-Taschenbuch", Carl Hanser Verlag, Munich/Vienna, 1981 and M. and J. Ash, "Encyclopedia of Surfactants", Vol I-111, Chemical Publishing Co., New York, 1980–81.

The herbicide formulations normally contain 0.1 to 99% by weight, especially 0.1 to 95% by weight of active ingredient mixture comprising the compounds of formulae II to VI with the compounds of formula I, 1 to 99.9% by weight of a solid or liquid formulation assistant and 0 to 25% by weight, especially 0.1 to 25% by weight of a surfactant.

While concentrated compositions are usually preferred as a commercial product, the final user normally uses diluted formulations.

The compositions may also contain further additives such as stabilizers, e.g. optionally epoxidated vegetable oils (epoxidated coconut oil, rapeseed oil or soybean oil), defoamers, e.g. silicone oil, preservatives, viscosity regulators, binding agents, adhesives, as well as fertilizers or other active ingredients.

In order to employ antidotes of formula I or compositions containing them for the protection of cultivated plants from the damaging activity of herbicides of formulae II to VI, various methods and techniques may be considered, for example the following ones:

I) Seed dressing a) Dressing the seeds with an active ingredient of formula I formulated as a wettable powder, by shaking in a vessel until evenly distributed on the seed surface (dry treatment). Here, about 1 to 500 g of active ingredient of formula I (4 g to 2 kg wettable powder) are used per 100 kg of seed grain.

b) Dressing the seeds with an emulsion concentrate of the active ingredient of formula I according to method a) (wet treatment).

c) Dressing by immersing the seed grain in a liquid with 100–1000 ppm active ingredient of formula I for I to 72 hours and optionally subsequently drying the seeds (dressing by immersion).

Dressing the seed grain or treatment of the germinated seedling are of course the preferred methods of application, since the treatment with active ingredient is aimed wholly at the target culture. It is customary to use 1 to 1000 g antidote, preferably 5 to 250 g antidote, per 100 kg seed grain, whereby depending on the method, which also enables other active ingredients or micro-nutrients to be added, deviations above or below the concentration limits indicated may be allowed (repeat dressing).

ii) Application as a tank miture

A liquid formulation of a mixture of antidote and herbicide (reciprocal ratio from 10:1 to 1 :100) is used, whereby the amount of herbicide applied is 0.005 to 5.0 kg per hectare. Such tank mixtures are applied before or after sowing.

iii) Application in the furrow

The antidote is applied to the open furrow as an emulsion concentrate, wettable powder or granulate. After covering the furrow, the herbicide is applied in the usual manner in a pre-emergence process.

iv) Controlled release of active ingredient

The active ingredient of formula I in solution is absorbed onto mineral granulate carriers or polyrnerised granulated materials (urealformaldehyde) and dried. If required, a coating may be applied (coated granules) which enables the active ingredient to be dispensed in a controlled release over a certain period.

The preferred formulations are made up in particular as follows:

(%=percent by weight)

Emulsifiable concentrates:

| | |
|---|---|
| active ingredient mixture: | 1 to 90%, preferably 5 to 20% |
| surface-active agent: | 1 to 30%, preferably 10 to 20% |
| liquid carrier: | 5 to 94%, preferably 70 to 85% |

-continued

| Dusts: | |
|---|---|
| active ingredient mixture: | 0.1 to 10%, preferably 0.1 to 5% |
| solid carrier: | 99.9 to 90%, preferably 99.9 to 99% |
| Suspension concentrates: | |
| active ingredient mixture: | 5 to 75%, preferably 10 to 50% |
| water: | 94 to 24%, preferably 88 to 30% |
| surface-active agent: | 1 to 40%, preferably 2 to 30% |
| Wettable powders: | |
| active ingredient mixture: | 0.5 to 90%, preferably 1 to 80% |
| surface-active agent: | 0.5 to 20%, preferably 1 to 15% |
| solid carrier material: | 5 to 95%, preferably 15 to 90% |
| Granulates: | |
| active ingredient mixture: | 0.1 to 30%, preferably 0.1 to 15% |
| solid carrier material: | 99.5 to 70%, preferably 97 to 85% |

The following examples illustrate the invention further without restricting it.

Formulation examples for mixtures comprising herbicides of formulae II to VI and antidotes of formula I (%=percent by weight)

| F1. Emulsion concentrates | a) | b) | c) | d) |
|---|---|---|---|---|
| active ingredient mixture of formula I and II, III, IV, V or VI | 5% | 10% | 25% | 50% |
| Ca dodecylbenzene sulphonate | 6% | 8% | 6% | 6% |
| castor oil polyglycol ether (36 mols EO) | 4% | — | 4% | 4% |
| octyphenol polyglycol ether (7–8 mols EO) | — | 4% | — | 2% |
| cyclohexanone | — | — | 10% | 20% |
| arom. hydrocarbon mixture C9–C12 | 85% | 78% | 55% | 16% |

Emulsions of each desired concentration may be produced from such concentrates by dilution with water.

| F2. Solutions | a) | b) | c) | d) |
|---|---|---|---|---|
| active ingredient mixture of formula I and II, III, IV, V or VI | 5% | 10% | 50% | 90% |
| 1-methoxy-3-(3-methoxy-propoxy)-propane | — | 20% | 20% | — |
| polyethylene glycol MW 400 | 20% | 10% | — | — |
| N-methyl-2-pyrrolidone | — | — | 30% | 10% |
| arom. hydrocarbon mixture $C_9$–$C_{12}$ | 75% | 60% | — | — |

The solutions are suitable for application in the form of the smallest droplets.

| F3. Wettable powders | a) | b) | c) | d) |
|---|---|---|---|---|
| active ingredient mixture of formula I and II, III, IV, V or VI | 5% | 25% | 50% | 80% |
| Na lignin sulphonate | 4% | — | 3% | — |
| Na lauryl sulphate | 2% | 3% | — | 4% |
| Na diisobutyl naphthalene sulphonate | — | 6% | 5% | 6% |
| octytphenyl polyglycol ether (7–8 mols EO) | — | 1% | 2% | — |
| highly disperse silicic acid | 1% | 3% | 5% | 10% |

-continued

| F3. Wettable powders | a) | b) | c) | d) |
|---|---|---|---|---|
| kaolin | 88% | 62% | 35% | — |

The active ingredient is mixed well with the adjuvants and ground well in an appropriate mill. Wettable powders are obtained, which may be diluted with water to suspensions of any desired concentration.

| F4. Coated granules | a) | b) | c) |
|---|---|---|---|
| active ingredient mixture of formula I and II, III, IV, V or VI | 0.1% | 5% | 15% |
| highly disperse silicic acid | 0.9% | 2% | 2% |
| inorg. carrier material (Ø 0.1–1 mm) such as $CaCO_3$ or $SiO_2$ | 99.0% | 93% | 83% |

The active ingredient is dissolved in methylene chloride, sprayed onto the carrier and the solvent subsequently evaporated in a vacuum.

| F5. Coated granules | a) | b) | c) |
|---|---|---|---|
| active ingredient mixture of formula I and II, III, IV, V or VI | 0.1% | 5% | 15% |
| polyethylene glycol MW 200 | 1.0% | 2% | 3% |
| highly disperse silicic acid | 0.9% | 1% | 2% |
| inorg. carrier material (Ø0.1–1 mm) such as $CaCO_3$ or $SiO_2$ | 98.0% | 92% | 80% |

The finely ground active ingredient is evenly applied in a mixer onto the carrier material which has been moistened with polyethylene glycol. In this way, dust-free coated granules are obtained.

| F6. Extension granules | a) | b) | c) | d) |
|---|---|---|---|---|
| active ingredient mixture of formula I and II, III, IV, V or VI | 0.1% | 3% | 5% | 15% |
| Na lignin sulphonate | 1.5% | 2% | 3% | 4% |
| carboxymethyl cellulose | 1.4% | 2% | 2% | 2% |
| kaolin | 97.0% | 93% | 90% | 79% |

The active ingredient is mixed with the additives, ground and moistened with water. This mixture is extruded and subsequently dried in a current of air.

| F7. Dusting agent | a) | b) | c) |
|---|---|---|---|
| active ingredient mixture of formula I and II, III, VI, V or VI | 0.1% | 1% | 5% |
| talc | 39.9% | 49% | 35% |
| kaolin | 60.0% | 50% | 60% |

By mixing the active ingredient with the carrier materials and grinding in an appropriate mill, a dusting agent is obtained which is ready for use.

| F8. Suspension concentrates | a) | b) | c) | d) |
|---|---|---|---|---|
| active ingredient mixture of formula I and II, III, IV, V or VI | 3% | 10% | 25% | 50% |
| ethylene glycol | 5% | 5% | 5% | 5% |
| nonylphenol polyglycol ether (15 mols EO) | — | 1% | 2% | — |
| Na lignin sulphonate | 3% | 3% | 4% | 5% |
| carboxymethyl cellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the additives. In this way, a suspension concentrate is obtained, from which suspensions of any desired concentration may be prepared by dilution with water.

It is often more practical to formulate the active ingredients of formulae II to VI and the mixture components of formula I individually and then, shortly prior to placing in the applicator, to bring them together in water in the desired mixture ratio as a "tank mixture".

The ability of the antidotes of formula I to protect cultivated plants from the phythotoxic activity of herbicides of formulae II to VI is illustrated in the following examples.

BIOLOGICAL EXAMPLES

Example B1

Post-emergent application of mixtures of a herbicide of formulae II to VI with an antidote of formula I on cereals.

Wheat is raised in small plastic pots under glasshouse conditions up to the 2–5 leaf stage. At this stage, the herbicides of formulae II to VI are applied to the test plants both on their own and in a mixture with an antidote of formula I. Application takes place as an aqueous suspension of the test substances (formulation example F8) with 500 l water/ha. The test is evaluated 21 days after application using a nine-stage appraisal scale (1=complete damage, 9=no effect). Appraisal marks of 1 to 4 (especially 1 to 3) indicate strong phytotoxic activity. Appraisal marks of 5–9 (especially 7–9) indicate little to no phytotoxic damage of useful plants.

The results obtained show that with the antidote (3-oxo-isochroman-4-ylidenemethoxy)-acetic acid methyl ester (compound no. 01.002), the damage caused to wheat by the herbicide clodinafop can be considerably reduced.

The same results are obtained if (3-oxo-isochroman-4-ylidenemethoxy)-acetic acid methyl ester (compound no. 01.002) and clodinafop are formulated according to examples F1 to F7.

Equally good results are obtained for the combinations (3-oxo-isochroman-4-ylidenemethoxy)-acetic acid methyl ester (compound no. 01.002) with primisulfuron, chlorimuron or with the compound of formula

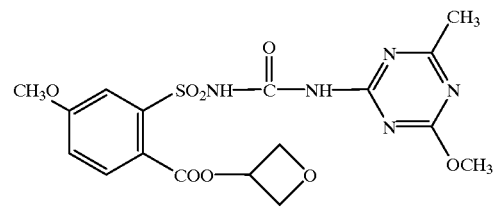

(IIIa)

or

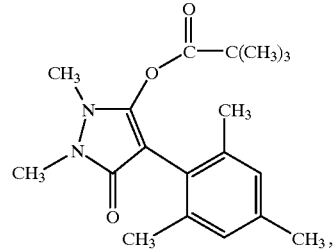

(Comp. No. 1.3)

as well as for the combinations (2-oxo-indan-1-ylidenemethoxy)-acetic acid methyl ester (compound no. 02.004) with clodinafop, primisuffuron, chlorimuron or with the compound of formula

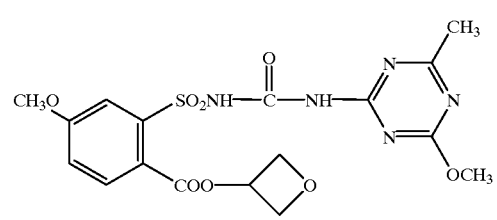

(IIIa)

or

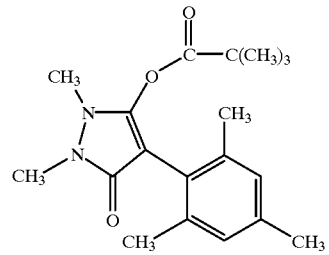

(Comp. No. 1.3)

The following Tables B1 to 85 illustrate the good antidote effect of the compounds of formula I[ in a mixture with the herbicides of formulae 11, 111 and VI.

TABLE B1

Post-emergent phytotoxic activity of the herbicides of formula II on the example clodinafop and the mixtures of clodinafop with antidotes of formula I on maize. The application rate for the herbicide clodinafop is 5 g/ha. The application rate for the antidotes of formula I is 250 g/ha.

| Herbicide [g/ha] | | antidote [g/ha] | phytotoxic activity: maize |
|---|---|---|---|
| Clodinafop | | — | 1 |
| Clodinafop | + | 02.011 | 6 |
| Clodinafop | | — | 2 |
| Clodinafop | + | 01.003 | 5 |
| Clodinafop | + | 01.005 | 7 |
| Clodinafop | + | 01.006 | 7 |
| Clodinafop | + | 02.004 | 9 |
| Clodinafop | + | 02.005 | 6 |
| Clodinafop | + | 03.003 | 9 |
| Clodinafop | + | 03.004 | 8 |
| Clodinafop | + | 03.006 | 6 |
| Clodinafop | | — | 3 |
| Clodinafop | + | 01.002 | 6 |
| Clodinafop | + | 02.001 | 6 |
| Clodinafop | + | 02.002 | 6 |
| Clodinafop | | — | 4 |
| Clodinafop | + | 01.007 | 9 |
| Clodinafop | + | 01.008 | 8 |
| Clodinafop | + | 01.012 | 7 |
| Clodinafop | + | 01.013 | 7 |
| Clodinafop | + | 04.004 | 7 |
| Clodinafop | + | 04.005 | 7 |

TABLE B2

Post-emergent phytotoxic activity of the herbicides of formula II on the example clodinafop and the mixtures of clodinafop with antidotes of formula I on rice. The application rate for the herbicide clodinafop is 60 g/ha. The application rate for the antidotes of formula 1 is 250 g/ha.

| Herbicide [g/ha] | | antidote [g/ha] | phytotoxic activity: rice |
|---|---|---|---|
| Clodinafop | | — | 2 |
| Clodinafop | + | 02.011 | 6 |
| Clodinafop | | — | 3 |
| Clodinafop | + | 01.006 | 6 |
| Clodinafop | | — | 4 |
| Clodinafop | + | 01.007 | 7 |
| Clodinafop | + | 04.003 | 6 |
| Clodinafop | + | 04.004 | 6 |
| Clodinafop | + | 04.005 | 6 |

TABLE B3

Post-emergent phytotoxic activity of the herbicides of formula III on the example of the compound of formula IIIa and the mixtures of compounds of formula IIIa with antidotes of formula on rice. The application rate for the herbicide IIIa is 125 g/ha. The application rate for the antidotes of formula I is 250 g/ha.

| Herbicide [g/ha] | | antidote [g/ha] | phytotoxic activity: rice |
|---|---|---|---|
| IIIa | | — | 3 |
| IIIa | + | 01.001 | 4 |
| IIIa | + | 01.003 | 5 |

TABLE B4

Post-emergent phytotoxic activity of the herbicides of formula III on the example of the compound of formula IIIe

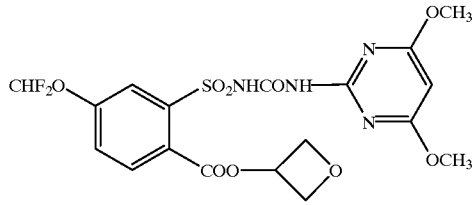

(IIIe)

and the mixtures of compounds of formula IIIe with antidotes of formula I on maize. The application rate for the herbicide IIIe is 25 g/ha. The application rate for the antidotes of formula I is 250 g/ha.

| Herbicide [g/ha] | | antidote [g/ha] | phytotoxic activity: maize |
|---|---|---|---|
| IIIe | | — | 3 |
| IIIe | + | 02.004 | 5 |
| IIIe | + | 03.004 | 6 |
| IIIe | | — | 4 |
| IIIe | + | 01.013 | 7 |
| IIIe | | — | 5 |
| IIIe | + | 02.009 | 7 |
| IIIe | + | 02.011 | 7 |

TABLE B5

Post-emergent phytotoxic activity of the herbicides of formula VI on the example of the compound aRS,1'S(-)N-(1'-methyl-2'-methoxyethyl)-N-chloracetyl-2-ethyl-6-methylaniline (VIa) and the mixtures of compound aRS,1'S(-)N-(1'-methyl-2'-methoxyethyl)-N-chloracetyl-2-ethyl-6-methylaniline (VIa) with antidotes of formula I on maize. The application rate for the herbicide VIa is 5 g/ha. The application rate for the antidotes of formula I is 250 g/ha.

| Herbicide [g/ha] | | antidote [g/ha] | phytotoxic activity: maize |
|---|---|---|---|
| VIa | | — | 3 |
| VIa | + | 01.002 | 5 |
| VIa | + | 02.004 | 5 |

What is claimed is:

1. A compound of formula I

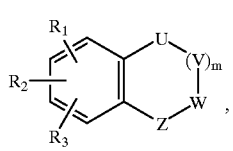

(I)

wherein $R_1$ is hydrogen, $C_1$–$C_4$-alkyl, $C_1$–$C_4$-alkyl substituted by $C_1$–$C_4$-alkyl-X- or $C_1$–$C_4$-halogen-alkyl-X-, $C_1$–$C_4$-haiogen-alkyl, nitro, cyano, —COOR$_8$,—NR$_p$R$_{10}$, —SO$_2$NR$_{11}$R$_{12}$ or CONR$_{13}$R$_{14}$;

$R_2$ is hydrogen, halogen, $C_1$–$C_4$-alkyl, trifluoromethyl, $C_1$–$C_4$-alkoxy or $C_1$–$C_4$-halogen-alkoxy;

$R_3$ is hydrogen, halogen or $C_1$–$C_4$-alkyl;
U is $C(R_{16})R_{16}$;
V is sulfur;
W is carbonyl;
Z is a group

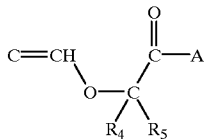

$R_4$ and $R_5$ independently of one another, signify hydrogen or $C_1$–$C_8$-alkyl; or
$R_4$ and $R_5$ together form a $C_2$–$C_8$-alkylene group;
A is $R_7Y$— or —$NR_{18}R_{19}$;
X is oxygen or $S(O)_p$;
Y is oxygen or suffur;
$R_7$ is hydrogen, $C_1$–$C_8$-alkyl, $C_1$–$C_8$-halogen-alkyl, $C_1$–$C_4$-alkoxy-$C_1$–$C_8$-alkyl, $C_3$–$C_8$-alkenyloxy-$C_1$–$C_8$-alkyl or phenyl-$C_1$–$C_8$-alkyl, whereby the phenyl ring may be substituted by halogen, $C_1$–$C_4$-alkyl, trifluoromethyl, methoxy or methyl—$S(O)_p$—; $C_3$–$C_6$-alkenyl, $C_3$–$C_6$-halogen-alkenyl, phenyl-$C_3$–$C_8$-alkenyl, $C_3$–$C_8$-alkinyl, or phenyl-$C_3C_6$-alkinyl;
$R_6$ is hydrogen or $C_1$–$C_4$-alkyl;
$R_9$ is hydrogen, $C_1$–$C_4$-alkyl or $C_1$–$C_4$-alkylcarbonyl;
$R_{10}$ is hydrogen or $C_1$–$C_4$-alkyl; or
$R_9$ and $R_{10}$ together form a $C_4$- or $C_8$-alkylene group;
$R_{11}$, $R_{12}$, $R_{13}$ and $R_{14}$, independently of one another, are hydrogen or $C_1$–$C_4$clkyl; or $R_{11}$ together with $R_{12}$ or $R_{13}$ together with $R_{14}$, independently of one another, are $C_4$- or $C_5$-alkylene, whereby one carbon atom may be replaced by oxygen or sulfur, or one or two carbon atoms may be replaced by —$NR_{1\,5}$—;
$R_{15}$ and $R_{16}$, independently of one another, are hydrogen or $C_1$–$C_8$-alkyl; or $R_{15}$, and $R_{16}$ together are $C_2$–$C_8$-alkylene;
$R_{19}$ is hydrogen, $C_1$–$C_8$-alkyl, phenyl, phenyl-$C_1$–$C_8$-alkyl, whereby the phenyl rings may be substituted by fluorine, chlorine, bromine, nitro, cyano, —$OCH_3$, $C_1$–$C_4$-alkyl or $CH_3SO_2$—; $C_1$–$C_{14}$-alkoxy-$C_1$–$C_8$-alkyl, $C_3$–$C_8$-alkenyl, $C_3$–$C_8$-alkinyl or $C_3$–$C_8$-cyloalkyl;
$R_{19}$ is hydrogen, $C_1$–$C_8$-alkyl, $C_3$–$C_6$-alkenyl or $C_3$–$C_8$-alkinyl; or
$R_{18}$ and $R_{19}$ together are $C_4$- or $C_8$-alkylone, whereby one carbon atom may be replaced by oxygen or sulfur, or one or two carbon atoms may be replaced by —$NR_{20}$—;
$R_{20}$ Is hydrogen or $C_1$–$C_4$-alkyl;
m is 1; and
p signifies 0, 1 or 2,
as well as agronomically compatible salts and stereodsomers of the compound.

2. The compound according to claim 1, wherein $R_{18}$ is hydrogen, $C_1$–$C_8$-alkyl, phenyl, phenyl-$C_1$–$C_8$-alkyl, whereby the phenyl rings may be substituted by fluorine, chlorine, bromine, nitro, cyano, —$OCH_3$, $C_1$–$C_4$-alkyl or $CH_3SO_2$—; $C_1$–$C_4$-alkoxy-$C_1$–$C_8$-alkyl, $C_3$–$C_6$-alkenyl, or $C_3$–$C_6$-alkinyl.

3. The compound according to claim 1, wherein $R_4$ and $R_5$ are hydrogen.

4. The compound according to claim 1, wherein A is $R_7$-$Y^4$.

5. The compound according to claim 4, wherein Y is oxygen.

6. The compound according to claim 1, wherein $R_{15}$ and $R_{16}$ signify hydrogen.

7. The compound according to claim 1, wherein $R_{15}$ and $R_{16}$ signify hydrogen; $R_7$ is methyl and Y is oxygen.

8. The compound according to claim 1, wherein $R_1$ to $R_5$, $R_{15}$ and $R_{16}$ are hydrogen, and A is $R_7$—Y—.

9. The compound according to claim 8, wherein $R_7$ is methyl and Y is oxygen.

10. A process for the production of compounds of formula I according to claim 1, which comprises reacting a compound of formula VIIa

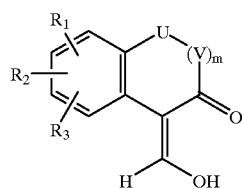

with a compound of formula X

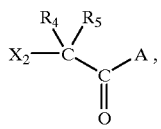

wherein $R_1$ to $R_3$, $R_4$, $R_5$ and A, U, V, and m are as defined in claim 1, and $X_2$ signifies a leaving group, a) in the presence of a base and an organic solvent at temperatures of 0° to 100° C., or
b) in the presence of an excess of cesium fluoride in an organic solvent at temperatures of 0° to 50° C.

11. A compound of formula VIIa$_1$

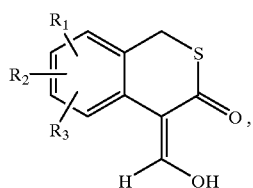

wherein $R_1$, $R_2$ and $R_3$ are as defined in claim 1.

12. A composition comprising one or more inert formulation assistants and a herbicidally effective amount of the compound of formula I according to claim 1.

13. A process for the production of compounds of formula VIIa where m is 1

(VIIa)
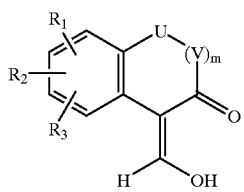
comprising reacting a compound of formula XIa
(XIa)
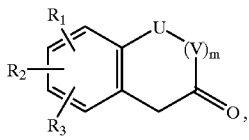
with a compound of formula VIII
(VIII)
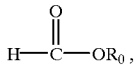
wherein $R_1$ to $R_3$, U, V and m are as defined in claim 1 and $R_0$ is $C_1$–$C_4$-alkyl, in the presence of a base and optionally an organic solvent.
* * * * *